US011414642B2

(12) United States Patent
Stobbe

(10) Patent No.: US 11,414,642 B2
(45) Date of Patent: Aug. 16, 2022

(54) DISPOSABLE BIOPROCESS SYSTEM SUPPORTING BIOLOGICAL ACTIVITY

(71) Applicant: STOBBE GMBH, Morbio Inferiore (CH)

(72) Inventor: Per Stobbe, Chiasso (CH)

(73) Assignee: STOBBE GMBH, Morbio Inferiore (CH)

( * ) Notice: Subject to any disclaimer, the term of this patent is extended or adjusted under 35 U.S.C. 154(b) by 461 days.

(21) Appl. No.: 15/750,938

(22) PCT Filed: May 17, 2016

(86) PCT No.: PCT/EP2016/061000
§ 371 (c)(1),
(2) Date: Feb. 7, 2018

(87) PCT Pub. No.: WO2017/025210
PCT Pub. Date: Feb. 16, 2017

(65) Prior Publication Data
US 2018/0237737 A1    Aug. 23, 2018

(30) Foreign Application Priority Data

Aug. 8, 2015 (DK) .............................. PA201500453

(51) Int. Cl.
*C12M 1/00* (2006.01)
*C12M 1/06* (2006.01)
*C12M 1/12* (2006.01)

(52) U.S. Cl.
CPC ............ *C12M 47/10* (2013.01); *C12M 23/28* (2013.01); *C12M 23/38* (2013.01); *C12M 23/40* (2013.01);
(Continued)

(58) Field of Classification Search
CPC ...... C12M 47/10; C12M 23/28; C12M 23/38; C12M 23/40; C12M 25/02; C12M 27/02;
(Continued)

(56) References Cited

U.S. PATENT DOCUMENTS 6,544,424 B1    4/2003 Shevitz
7,425,441 B2    9/2008 Broneske et al.
(Continued)

FOREIGN PATENT DOCUMENTS

CN    102559480 A    7/2012
EP    0995483 A1    4/2000
(Continued)

OTHER PUBLICATIONS

International Search Report dated Aug. 22, 2016 of corresponding International application No. PCT/EP2016/061000; 4 pgs.

*Primary Examiner* — William H. Beisner
*Assistant Examiner* — Danielle B Henkel
(74) *Attorney, Agent, or Firm* — Maier & Maier, PLLC

(57) ABSTRACT

Embodiments of the invention relate to a Disposable Bioprocess System including a Single-Use-Bioreactor, a Single-Use-Pump and a single-use micro-organism retention filter. Combined most suitable for cultivation of suspended micro-organisms in a liquid media at high micro-organism concentration in a perfusion mode continuous process for expression of biological material. The inlet port of the liquid Single-Use-Pump connects via a valve to the broth reservoir of the Single-Use-Bioreactor through a liquid conveying port. The outlet port of the liquid pumping Single-Use-Pump connects via a valve to a micro-organism retention filter. And a method for operating said sterile Disposable Bioprocess System in perfusion mode for continuously processing.

22 Claims, 8 Drawing Sheets

(52) U.S. Cl.
CPC ............ *C12M 25/02* (2013.01); *C12M 27/02* (2013.01); *C12M 29/00* (2013.01); *C12M 29/04* (2013.01); *C12M 29/10* (2013.01); *C12M 29/18* (2013.01); *C12M 29/26* (2013.01); *C12M 37/04* (2013.01)

(58) Field of Classification Search
CPC ...... C12M 29/00; C12M 29/04; C12M 29/10; C12M 29/18; C12M 29/26; C12M 37/04
See application file for complete search history.

(56) References Cited

U.S. PATENT DOCUMENTS

| | | | |
|---|---|---|---|
| 2003/0036192 A1* | 2/2003 | Singh | .................... C12M 27/16 435/297.2 |
| 2008/0131957 A1 | 6/2008 | Ryan et al. | |
| 2009/0311776 A1 | 12/2009 | Kelly, Jr. et al. | |
| 2012/0077243 A1* | 3/2012 | Niazi | .................... C12M 23/26 435/170 |
| 2014/0154795 A1 | 6/2014 | Lipkens et al. | |

FOREIGN PATENT DOCUMENTS

| | | | |
|---|---|---|---|
| EP | 2141224 | A1 | 1/2010 |
| EP | 2674479 | A1 | 12/2013 |
| EP | 2674480 | A1 | 12/2013 |
| WO | 2010/055143 | A2 | 5/2010 |
| WO | 2011130617 | A2 | 10/2011 |

\* cited by examiner

DISPOSABLE BIOPROCESS SYSTEM SUPPORTING BIOLOGICAL ACTIVITY

TECHNICAL FIELD

Embodiments of the invention relate to a Disposable Bioprocess System including a Single-Use-Bioreactor, a single-use pumping device, and a single-use micro-organisms retention filter. Combined most suitable for cultivation of suspended micro-organisms in a liquid media at high micro-organism concentration for expression of biological material and methods for operating said Disposable Bioprocess System in a continuous process.

BACKGROUND OF THE INVENTION

In pharmaceutical bioreactors and fermenters, the goal is to cultivate or ferment micro-organisms for production of biological materials or biomass for medical applications. Such as regenerative medicine and therapeutic applications or drugs or more traditional expression from living cells or micro-organisms of molecules for therapeutic purposes or as drugs.

The re-usable, non-disposable Stirred-Tank-Reactors (STR) being either a bioreactor or fermenter is of the size from less than one liter to more than 200 liter and formed of Stainless Steel and high quality glass. Typical volumes for lab scale STR versions are 1-20 liter comprising a glass housing/container hanging under a removable Stainless Steel head plate and the entire STR suspending in a three-leg metal structure. The head plate contains ports for sensors, sampling, gas exchange, media exchange, and a centrally oriented shaft for external mounted servo motor connection in order to insure media agitation inside the STR. Temperature are adjusted by an electrical heating blanket or water jacketing of the STR.

The disposable Stirred-Tank-Reactor were considered a novelty, and perhaps even a passing trend, as recent as mid 90ties. As the Single-Use-Bioreactors (SUB) have matured, their market acceptance for single-use equipment in general has rapidly expanded. The move to disposable production equipment is, in many instances, driven by cross contamination problems, cost reduction in steam sterilization and cleaning requirements, improved plant flexibility, reduced costs and faster time to market for the end product.

BACKGROUND ART

US 2009/0311776 and EP2141224 both from Millipore Corp describes a pre-sterilized, disposable bioreactor made of two parts being the rigid plastic top cover and a rigid plastic body with one or more fluid ports in the housing body, said top cover integrates the sensor ports and all the ports having a cap;

US 2008/0131957 from Corning Inc—disposable symmetrical cylindrical plastic spinner flask container with impeller on flexible axle, three container wall integrated baffles creating turbulence and a cover with no sensor ports;

New Brunswick Scientific fermenter housing body model BioFlo310 consist of a metal jacketed bottom assembly, a glass cylinder and a metal head plate. All ports except the two water heating/cooling ports are arranged in the head plate. Further the drive motor is arranged in the head plate;

U.S. Pat. No. 6,544,424 from Refined Technology Co. expose a liquid filtration system comprising a cultivating storage container, a hollow fiber filter module and a diaphragm pump performing combined as a cell retention system for high cell density cultivation in which the pumping device operate without valves in an alternating manner for media recirculation;

WO 2010055143 from Artelis S. A. describes a disposable culture housing body with at least one external wall integrating a sensor a culture zone and a transfer zone performing as a cell retention system with high cell density and a centrifugal pump for media recirculation;

U.S. Pat. No. 7,425,441 from Sartorius Stedim Biotech GmbH describes a bioreactor with next to culturing container one or more aeration tubes with injectors arranged;

EP 2674480 from DASGIP Information and Process Technology GmbH describes small disposable bioreactors (STR) designed to fit in a parallel block (shown in FIG. 5). The product Bioblock perform the temperature control and alternatively also drive of the stirring or agitation device. The Bioblock is designed to operate 4 STRs or SUBs in parallel encapsulating the bottom part of the STR container.

Operating the Stirred-Tank-Reactor in semi continuous process mode/perfusion mode at high cell density requires additional techniques and equipment such as a cell retention system. Combining the Stirred-Tank-Reactor with an externally arranged, stand-alone and alternate flow direction pump and a Cross-Flow-Filter device has proved well offering medium to high cell density and weeks of perfusion mode operation. Well known and dominating in the industry as ATF, the Alternating-Tangential-Flow concept by Refined Technology in New Jersey, USA allowing high cell numbers and cell free product harvest. All ATF offered are of re-usable stainless steel and glass design and not available as single-use complete setup.

Increasing need from the industry for Continuous Processing and fast multiple tests has quite surprising not promoted development of the Stirred-Tank-Reactor integrating pump and cell retention system in an all pre-sterilized single-use packages. The industry is at present stocked with traditional ATF based on glass and steel requiring subsequent frequent time consuming and costly steam sterilization.

Any re-use of STR or ATF parts required to be sterile involve the subject of contamination and loss of costly culture.

Definitions relevant for the present invention:

The term "a" or "an" as used herein means one or more or at least one.

The term "alternating" as used herein describes a liquid flow of bi-directional direction. One specific and identical volume moving forth and backwards, no valves for flow direction control is included.

The term "ATF" as used by the industry and herein means Alternating-Tangential-Flow which is a concept where the pumps specific volume is constant and this volume is alternating, changed back and forth (forward and reverse), the diaphragm can only move between two end positions, no new, fresh liquid or broth is added directly to the pump, no valves are included.

The term "backflow" is used to describe a slight harvest return flow, increasing the TMP, Trans Membrane-Pressure somewhat helping high velocity flow along the membrane to remove deposits. Backflow not to be confused with the term "backflush" being widely used in the (rigid) membrane industry though not feasible on elastic membranes such as "hollow fibre module".

The term "batch operation" as used herein refers to an operation method with constant WV and to which no fresh media is added and no used media and/or liquid removed, typically lasting less than one week when cultivating micro-organisms such as CHO cells.

The term "biological material" as used herein describes organic compounds, tissue, cellular components, body compatible fluids, biomass, bio-composites, biocompatible materials, antibodies in general, DNA, RNA, proteins, molecules for therapeutic purposes and the like.

The term "bioreactor" as used herein means a physical device, which biologically active environment is suitable for cultivation of micro-organism performing a desired process suspended in liquid media agitated by an impeller.

The term "broth" as used herein means the non-filtered liquid content, the cultivation soup in a fermenter or bioreactor consisting of cells, debris, micro-organisms, media with nutrients, waste, harvest, etc. The broth, feedstock enters the CFF and pass the Cross-Flow-Filter membrane whereby the broth becomes slightly concentrated retentate at the CFF exit and as such is returned into and re-mixed with the broth in the bioreactor.

The term "CHO" refers to Chinese Hamster Ovary cells being a "micro-organism" and mammalian cell line very popular as expression platform of proteins for the pharma industry.

The term "container" as used herein means a hollow housing, a body with an internal reservoir, which may be open or closed, such as without limitation a beaker, a flask, a bottle, a tube, a vessel, a tank, a polymeric material film bag with a wall forming the reservoir. The container when operating as for instance a Stirred-Tank-Reactor is typically arranged with a vertical wall and a horizontal bottom wall pointing down wards, so that liquid or fluid in the container is predominantly maintained inside the container during operation mode. The container may be of cylindrical design, or non-cylindrical design such as conical design or of square box shaped design, a flexible film bag or combinations hereof. The container may enclose or surround a SUB, a SUP, a CFF.

The term "Container Volume" (CV) as used herein refer to total volume of the housing body when used as a bioreactor or a fermenter or a mixer.

The term "Cross-Flow-Filter" (CFF) as used herein is a filter device, a separating device which allow a liquid and in liquid suspended selectable components to pass the separating device with the liquid volume onto the other side of the device by crossing, passing the device with certain specification eliminating desired suspended components not to pass the separating device. The device has a first entrance for the broth and a second exit for the retentate. In between the broth first entrance and the retentate second exit further a third permeate exit for the product, the filtrate, the harvest which has passed the device.

The term "cultivation" or "culturing" refers to hosting of micro-organism, such as mammalian cells, in a bioreactor for production purposes, such as expression of a product by said micro-organisms or proliferation of said micro-organisms The term "deposit" or "membrane coating" or "filter cake" as used herein refers to a process where solute, particles, micro-organisms deposit onto a membrane surface, such as a Cross-Flow-Filter membrane surface or even into membrane pores in a way that degrades the membrane's performance and increase transmembrane pressure to undesired levels. Such deposit may be removed by increased shear force such as high velocity of the re-circulating broth for washing purposes.

The term "diaphragm" as used herein is a round, somewhat dome shaped sheet of rubber material preferably with a sealing arrangement on the circumference. The diaphragm operates inside a housing and separate the wetted side with broth from the SUB from the drive fluid side.

The term "disposable" refers to a product manufactured often from synthetic materials preferably at low cost and to be scrapped after use. The here presented Disposable Bioreactor System is further bagged and pre-sterilized ready for use.

The term "exterior facility" (area) means laboratory, production facility, testing facility in which room(s) the Disposable Bioprocess System is in use. In the exterior facility also the down-stream process may take place.

The term "fed-batch" operation as used herein refers to a bioreactor or fermenter which start the process with a minimum media volume to which fresh medium is added and no liquid removed until after termination of the process. A minimum of media volume in the housing body are inoculated with micro-organism and appear as seed train until the maximum WV is reached prior to process termination. Typical operation time is 2-3 times longer than batch operation.

The term "fermenter" as used herein means a physical device, a container, suitable for fermentation of micro-organism performing a fermentation process when suspended in liquid media and agitated by a turbine.

The term "fermentation" as used herein refers to hosting of micro-organisms, such as living single-celled organisms, prokaryotes, bacteria for industrial purposes in a fermenter expressing a product.

The term "filter device" as used here in refer to a Cross-Flow-Filter as mentioned as a CFF.

The term "fluid" refers to a gas or a liquid, a gas such as air or nitrogen at variable volume or a liquid such as water and/or oil at constant volume or a mixture of gases and liquids.

The term "glass" as used herein refers to transparent silica based amorphous brittle and solid material often with excellent corrosion resistance.

The term "harvest" as used herein refer to the product part (such as a protein) of the broth being the expected product generated by micro-organism being cultivated in a bioreactor or fermented in a fermenter. The harvest (the filtrate, the permeate) may be separated from the broth via membrane and or CFF filtration. When permeate is removed from the CFF the broth is then concentrated.

The term "hollow fibre module" as used herein refer to a device made from an outer rigid wall tube with end covers housing inside a bundle of thin wall tubes fabricated from porous elastic material such as polyethersulfone or other polymers. The bundle of tubes are sealed, cast into end covers separating the tube inside from the tube outside and hereby appearing as a Cross-Flow-Filter.

The term "impeller" refers to a low speed fluid-agitating device equipped with blades or vanes rotating inside a liquid filled container for agitation, mixing, pumping, liquid circulation purposes.

The term "liquid suction tube" as used herein refer to a liquid inlet, a pipe or a tube sucking, conveying the broth from the container. The liquid suction tube convey liquid to the inlet of the pumping device passing an inlet valve.

The terms "media", "growth media", and "nutrient" as used herein are used interchangeable and refers to a sterile complex mixture containing mostly water, carbon sources, various gases such as oxygen and additives such as; vitamins, hormones, growth factors, animal serum, antibiotics, antioxidants, antifoams, cell stabilizers and other components for cultivation of "micro-organisms". Some media are serum based, some are serum free, animal free, and protein free or chemically defined media. During cultivation the combined media and micro-organism and various debris is named "broth".

The term "membrane" refers to a boundary layer, which serves as a selective barrier and remains impermeable to specific or desired particles, molecules, or substances when exposed to the action of a driving force (like supplied by a pump). Porous membranes are manufactured from a variety of flexible and rigid materials such as polymers, ceramics and metals. Appear further in the technical term "Cross-Flow-Filter (CFF) device". The membrane clarify a part of the broth know as harvest.

The term "membrane fouling" as used herein refer to the effect when solids, cells, cell parts, cell membranes, aggregates, etc creates a layer, a biofilm, a cake of debris on the porous membrane inlet surface. This effect requires higher TMP in order to overcome the increased resistance on the combined membrane and deposits and keep if desired constant flux. Membrane deposits can be removed by high shear forces, high broth velocity and/or backflush.

The term "micro-carrier" refer to a micro-organism supporting device or growth bodies allowing cultivation of adherent depending micro-organisms. Size range typical from 100 to 1.000 μm composed by gelatine, collagen, cellulose or polymeric materials or glass and may further be functionalized with one or more coatings.

The terms "micro-organism" or "cells" or "biological cells" as used herein are used interchangeable and is typically divided into: 1. living single-celled organisms, microbes such as; fungus, algae, moss, plankton, yeast, protozoa, eukaryotes, archaea, micro animals, extremophiles and plant cells or the like—2. adherent or semi adherent or suspended living cells such as animal cells, insect cells, mammalian cells, human cells, stem cells—3. prokaryotes and a variety of bacteria such as E. coli or the like—most of the above genetically modified to solve specific tasks and product needs.

The term "perfusion" or "cell/micro-organism retention perfusion" mode operation as used herein refers to the operation method or principle for a STR, SUB where the media is sequentially exchanged, fresh nutrients sequentially added, used media/harvest removed throughout the culture period. The micro-organisms retained in the STR, SUB last typically 4-8 times longer than batch and 2-4 times longer fed-batch.

The term "permeate" as used herein refers to specific parts of a mixture, the broth, a feedstock allowed to pass through a membrane. Also known as filtrate.

The term "permeable membrane" as used herein refer to a porous wall, a "membrane" allowing a liquid and selected particles (size separation) to pass the membrane and certain particles not to pass the porous wall, barrier, separation wall.

The term "ports" as used herein refers to holes anywhere in a wall allowing to attachment of suitable fittings or relevant sensors or general connections selected from the group of; PG 13.5 thread ports, locking ports, press-in ports, or ports involving Luer-Loc fitting, connecting fittings, sterile fittings, hoses, tubes, hose barbs, etc.

The term "PG 13.5" is a classical sensor (RUS) or port with a threaded mechanical connector. PG is the technical standard term known as Stahl-Panzer-Rohr-Gewinde.

The term "PCS" or "Process-Control-System" as used herein refer to a Programmable Logic Control (PLC), a Personal Computer (PC) an Embedded Computer (EC) both integrating a Central-Processing-Unit (CPU) electronic device with calculating power. The PLC has various Input & Output (I/O) with input from various sensors and output for various actuators for process control purposes. The PCS integrate software, algorithms, process recipe in build-in memory for managing, analysis of the cultivation or fermentation process for on-going process alignment according to the process recipe. The PCS correspond with a variety of sensors and actuators in order to alter the process parameters.

The term "PTF" as used herein refer to the new industrial terminology and means Pulsating-Tangential-Flow being the here presented invention. The PFT process involves a pump with a first inlet valve and a second outlet valve in order to insure one-directional liquid flow through the CFF.

The term "retentate" as used herein refers to the parts, micro-carriers, particles, "micro-organisms", debris of a mixture within the broth, feedstock that is held back by a "membrane", and do not pass the membrane as to its size, shape or charge.

The term "scalable" as used herein refers to the feature when CV and WV is not locked into fixed glass container dimensions. Further refer to that the ratio between container diameter and height can be altered accommodating end-user requirements.

The term "sensor" as used here refers to devices able to measure on-line quality process variables associated within a given process, such as the level of pH, dissolved oxygen (DO), bio mass/cell density, capacitance, conductivity, dissolved carbon dioxide, lactate, glucose, glutamine, glutamate, ammonia, pressure, liquid level, fluid mass-flow, velocity, temperature, viscosity, etc. Sensor to measure SUP performance may be proximity, distance being mechanical, optical, electrical (such as triangular laser sensor, a pressure sensitive level sensor, or capacitance or ultra-sonic based distance sensors). Sensors in general available as either Re-Useable-Sensors or Single-Use-Sensors.

The term "single-use" as used herein refers to a product designed for use only once and to be disposed after use typically delivered "sterilized" and ready to use, such as the "Single-Use-Bioreactor" (SUB) and "Single-Use-Sensors" (SUS).

The term "Single-Use-Sensors" (SUS) as used herein refer to a disposable devices able to on-line measure analysts, process conditions, fluid concentrations and deliver a signal, such as an electrical signal relative to the concentration measured. The in-expensive SUS body is designed primarily from polymeric materials to be pre-installed in a SUB or SUF for simultaneous sterilization all enclosed in dual or triple film bags for convenience to the end-user who then avoid sterilization before use.

The term "Single-Use-Bioreactor" (SUB) as used herein refer to film bag(s) including STR or bioreactor or Single-Use-Fermenter and preferable pre-installed with a pumping device and one or more "Single-Use-Sensors" all manufactured from disposable materials and sterilized and hereby ready for use eliminating the traditional in-house heat sterilization.

The term "Single-Use-Pump" (SUP) as used herein refer to a fluid conveying device manufactured at least partly from disposable materials. Such as a peristaltic pump or a centrifugal pump or a tube pump or a diaphragm pump or a piston pump or a direct gas-to-liquid surface driven air column pump or the like comprising disposable wetted part and re-usable non-wetted parts and a valve for flow direction control.

The term "Stainless Steel" as used herein refers to an alloyed metal based mostly on nickel, chromium, vanadium, carbon, and steel characterized with at least excellent corrosion resistance.

The term "sterilization" as used herein refer to any process that eliminates (removes) or kills (deactivates) all forms of life and other biological agents. Sterilization can be achieved with one or more of the following: heat, chemicals, irradiation, high pressure, and filtration.

The term "sterilized" as used herein refers to a product enclosed in a plastic film bags and exposed to sterilization methods which insure the bag content is sterile. The product is supplied in said film bag(s) to the end-user ready to open and use. The end-user hereby avoids the troublesome heat sterilization similar to classical re-usable equipment processed in an autoclave.

The term "Stirred-Tank-Reactor" (STR) is a widely used expression and as used herein refer to a bioreactor or fermenter with a "Container Volume" (CV) integrating an aeration device and agitation or mixing device(s) for forced exchange of nutrient and gas with the "microorganisms" within said media. STR are manufactured predominantly from stainless steel and glass.

The term "suspension" or "suspended" as used herein refers to particles, artificial particles, micro-carriers, micro-organism depending on being preferably homogeneous suspended or mobilized in liquid (in the broth) in the STR or SUB or "container".

The term "Tangential Flow Filter" (TFF) as used herein is a device which allow selectable components under pressure to pass from one liquid volume into another liquid volume crossing a "membrane" (cross-flow-filter) eliminating some components to pass the membrane. Such membranes or filter devices may be based on screens, porous material sheets integrated into cassettes or shaped as flat or round plate, tubes, corrugated tubes or stacked hollow fibres into a cartridge.

The term "top cover" as used herein refers to the upper, typically head plate, such as flat metal disc for the classical STR. The top cover is without limitation selected from the dominant Stainless Steel/glass STR design supplied by Sartorius, Applikon, Finesse, Broadley-James and app 20 other suppliers since the 70ties. Number of PG 13.5 ports available effected by the top cover diameter and in general being three to four ports. The top cover may take other shapes than the flat disc and be equipped with one or more ports.

The term "TMP" or "Trans-Membrane-Pressure" as used herein describes an excellent indicator of membrane fouling. Accumulated cells, debris, particles on the membrane surface. TMP increases to compensate for the membrane fouling at constant flux.

The term "Working Volume" (WV) as used herein refers to the media volume, process fluid, the broth in which the cultivation takes place inside the STR or SUB. Further the "head space volume"+Working Volume=Container Volume (CV).

SHORT PRESENTATION OF THE INVENTION

Figure 1:
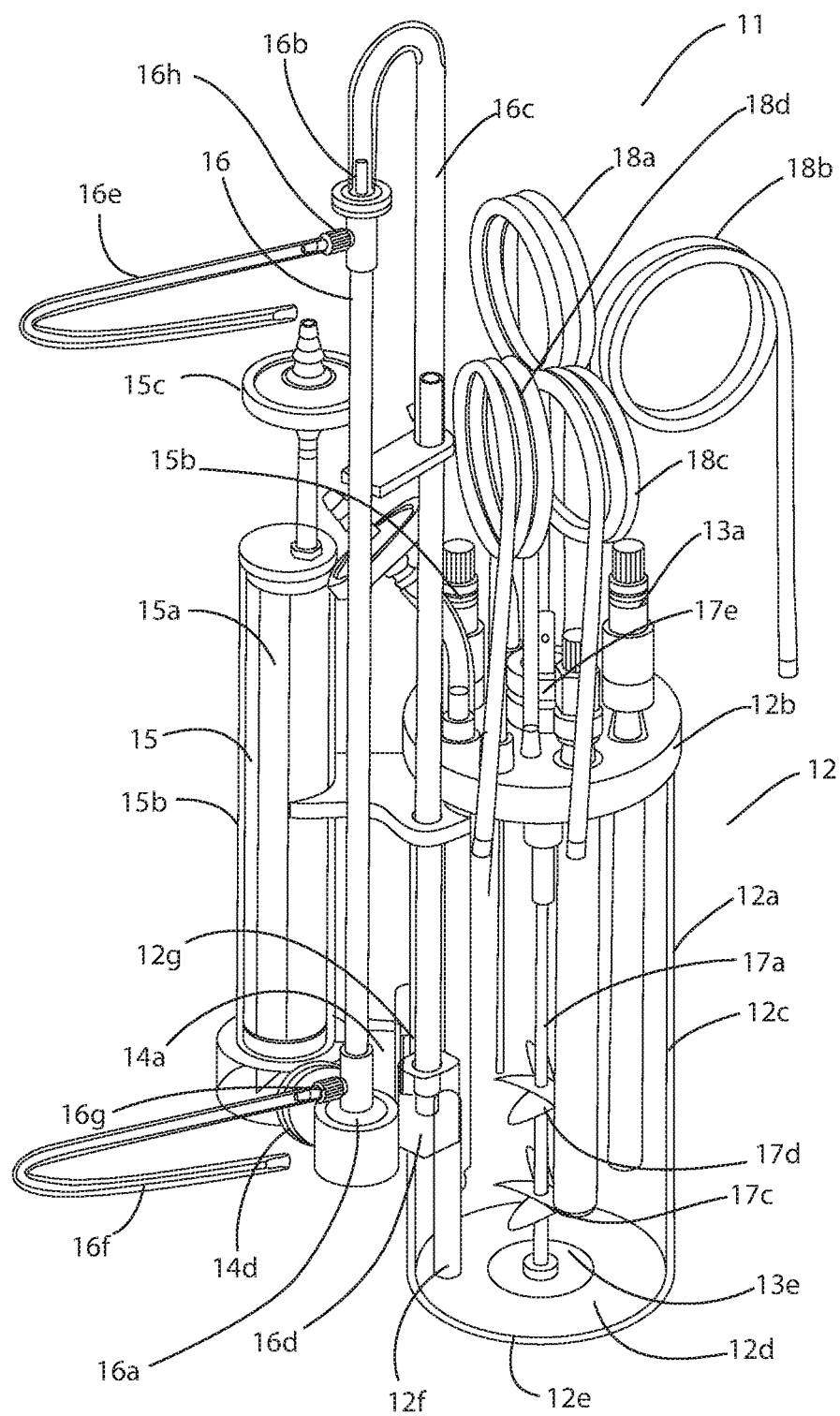
FIG. 1 show the complete PTF operating SUB with a SUP and a CFF integrated

The present invention relates to a Disposable Bioprocess System supporting biological activity comprising a fluid tight container comprising a process liquid broth volume surrounded by walls separating an interior process liquid volume from an exterior facility area wherein said process liquid volume communicates with a first liquid valve and a conveying liquid pumping device for pumping the process liquid in one direction away from the interior process liquid volume, and a second liquid valve and a filter device separating the interior process liquid volume from the exterior facility area wherein means of liquid communication from the interior process liquid volume of said fluid tight container to said liquid pumping device a further means of non-filtered liquid communication extends from said pumping device to a non-filtered first liquid communication port of said filter device, and further means for non-filtered retentate liquid re-circulated via a second liquid communication port of said filter back to the interior process liquid volume of said container, said filter device comprises at least one third permeate outlet port for conveying filtered process liquid to said exterior facility area as harvested product wherein the first liquid valve controls the communication between the interior process liquid volume and the pumping device, wherein the second liquid valve controls the communication between the pumping device and the filter device, and wherein a filter outlet port communicate between the filter device and the exterior facility area.

DETAILED PRESENTATION OF THE INVENTION

It is an object of the present invention to provide a Disposable Bioprocess System supporting biological activity comprising: a fluid tight container comprising a process liquid broth volume surrounded by walls separating an interior process liquid volume from an exterior facility area wherein said process liquid volume communicates with a first liquid valve and a conveying liquid pumping device for pumping the process liquid in one direction away from the interior process liquid volume, and a second liquid valve and a filter device separating the interior process liquid volume from the exterior facility area wherein means of liquid communication from the interior process liquid volume (12d) of said fluid tight container (12a) to said liquid pumping device (15) a further means of non-filtered liquid communication extends from said pumping device (15) to a non-filtered first liquid communication port of said filter device (16), and further means for non-filtered retentate liquid re-circulated via a second liquid communication port (16a) of said filter device back to the interior process liquid volume of said container, said filter device comprises at least one third permeate outlet port (16d, 16e) for conveying filtered process liquid to said exterior facility area as harvested product;
wherein the first liquid valve controls the communication between the interior process liquid volume and the pumping device, wherein the second liquid valve controls the communication between the pumping device and the filter device, and wherein a filter device outlet port communicate between the filter device and the exterior facility area.

The presented invention is a Disposable Bioprocess System for Continuous Processing of micro-organisms in the pharmaceutical industry integrating a Single-Use-Bioreactor (SUB), a Single-Use-Pump (SUP) and a single-use CFF based micro-organism retention device. Operating after the term Pulsating-Tangential-Flow, PTF of the Disposable Bioprocess System offer end-user benefits, freedom and features such as:

- Eliminate traditional time consuming steam sterilization as the PTF invention is pre-assembled, pre-sterilized with all necessary components ready for use right out of the box for lower cost of use and higher throughput in laboratories;
- Eliminate cross contamination as to the pre-assembled and pre-sterilized concept beneficial to both Research & Development as well full scale production;
- Minimizes installment time as the PTF cell retention system integrate the SUP and CFF either inside the SUB or outside of the SUB container, which also allow installment in parallel block's or robotic devices for desired perfusion mode processes;
- Un-parallel control of broth velocities and volume through the CFF for different harvest and cleaning cycles by a sensor measuring on-line liquid level (potentially separated by a diaphragm or piston) inside the SUP;
- The Disposable Bioprocess System enables rapid evaluation of multiple micro-organism cultures, increasing productivity in cell line development with significant savings on materials and labour.

The pharmaceutical industry desires a SUB platform supporting increased volumetric efficiency, more on-line analyst measures all in a single-use design with capability intended for micro-organism retention in perfusion mode operation. Potentially in parallel processing with semi-automated robots such as the DASGIP parallel operating Bioblock or the fully automated TAP Biosystem (from now Sartorius Stedim Biotech) or individually performing the continuous processing. For reasons unknown such Disposable Bioprocess System product as presented here does not exist today.

The present invention relates to a Disposable Bioprocess System comprising a SUB for cultivation or a SUF for fermenting of biomass and selected components comprising advantages (below briefly described) such as;

- A container comprising a range of ports, mechanical connected with or an integrated part of a hollow plastic container with an interior reservoir optionally with one or more side wall ports. The container have selectable diameter or cross section (such as round, cylindrical or non-cylindrical such as square design) and heights offering a desired interior reservoir and respective volume;
- Optionally a draft tube stator arranged vertical inside said container operating with none or one or more baffles arranged perpendicular and radially to said draft tube stator exterior space said draft tube stator having an interior space housing fluid motion, agitation means. The interior reservoir fluid agitation device(s) create a radial swirl of media which the tube stator convert into axial fluid movement and more efficient mixing axial vortexes;
- Optionally a baffle arranged vertical inside said container operating as a SUB extending inwards from the container side wall;
- A fluid motion, agitating device arranged on a rotating shaft attached to component comprising magnets and a bearing in contact with the container bottom for magnetic power transfer through the bottom wall driven by external magnetic means;
- A fluid motion, agitation device arranged on a rotating shaft penetrating the container top via a bearing/sealing arrangements for kinetic power input;
- A tube arranged vertical inside said container with the purpose of supplying a mixed gas addition to insure for the cells safe aeration;
- Liquid communication between the broth of the container and a Single-Use-Pump device, said SUP devise a liquid conveying or/and liquid direction control device in order to facilitate the pumping operation. Said SUP device may be arranged inside the container or external to the container;
- Liquid communication between the container a single-use Cross-Flow-Filter devices, said CFF devise and one or more liquid conveying or/and pumping devices and liquid direction control devices in order to facilitate the advantageous micro-organism retention under perfusion mode operation. Said CFF device(s) may be arranged inside the container and/or external to the container;
- Manufactured from materials considered to be disposable and supplied sterilized to the end-user for cost efficient single-use applications.

Dimension of the SUB container are not limited by, but may correspond the preferred dimension of the Bioblock or robot assembly to which the STR may be installed in. The container provides an interior space with exterior walls and two in principle flat end covers being top cover and bottom cover. Dimension of the container, housing assembly range 10 to 500 mm in diameter such as 20 to 200 mm and height from 10 to 1.000 mm such as 50 to 500 mm. Or measured in container cross section from 1 to 2.000 cm2. Or measured in CV ranging few millilitre up to 2.000 liter.

The invented Disposable Bioprocess System further comprise a variety of additional arranged devices and features in order to expand the simple batch operation to the more advantageous perfusion mode operation. Such as one or more; hollow bodies appearing as reservoirs, Cross-Flow- Filter devices, aeration devices, instrumentation, sensors, liquid conveying devices, valves, actuators, fluid accumulators and the like for regulating process means.

In addition the invented Disposable Bioprocess System comprises a Single-Use-Bioreactor a liquid conveying or pumping device and a Cross-Flow-Filter device for micro-organism retention perfusion mode operation. Such CFF may be manufactured from rigid porous ceramic support integrating a thin micro-porous membrane into a honeycomb module or manufactured from flexible semi-permeable flat or round membranes or hollow fibers bundled into a cartridge. The CFF are arranged in liquid contact with the process liquid broth either inside of the SUB or outside of or next to the SUB either above or next to the SUB with drainage from the SUB either above or below the container broth level. The CFF are sequentially exposed to liquid feed drawn by a liquid conveying device from the SUB process liquid reservoir through valve means into and occupying the entire interior, retentate compartment of the CFF retentate channels. After partly or fully closing of both liquid conveying inlet and CFF outlet valves the liquid conveying creates TMP across the CFF membrane. Which allows at least a part of the expressed and desired protein product from the processes suspended in the media to pass over the membrane and hereby be converted to permeate, harvest. The remaining micro-organism rich liquids and suspended debris inside the CFF are simultaneously converted to retentate and returned by flushing through CFF exit to the reservoir by suitable velocity for the liquid conveying operation.

The permeate side of the CFF may preferably be exposed to a pressure below the retentate liquid pressure in order to overcome the TMP losses. In fact—its preferred that a force on the permeate side helps overcome the TMP of the semi-permeable membrane as limited liquids pass the membrane mostly caused by a membrane fouling, deposits typically created from the broth on the retentate side of the CFF.

The present invented Disposable Bioprocess System supports numerous requirements and facilitate a variety of rigid or semi-rigid or flexible products used for fabrication of basic parts. Materials such as polymers to form one or more parts of the invention are, but not limited to materials such as; polycarbonates, polyesters, nylons, polyamide, PTFE resins and other fluoropolymers, acrylic and methacrylic resins and copolymers, polysulphones, polyethersulphones, polyarylsulphones, polystyrenes, polyetherimides, polyethylene terephthalates, polyvinyl chlorides, chlorinated polyvinyl chlorides, ABS and its alloys and blends, polyolefins, preferably polyethylenes such as linear low density polyethylene, low density polyethylene, high density polyethylene, and ultrahigh molecular weight polyethylene and copolymers thereof, polypropylene and copolymers thereof and metallocene generated polyolefins. Or partly, semi rigid materials such as silicone, rubber and otherwise elastic materials.

The basic individual parts of the container manufactured by or assembled from:
injection moulding or blow moulding or vacuum-thermo shaping of basic parts;
welding basic parts together;
moulding basic part pieces together via injection moulding process;
sealing of basic parts between assembling surfaces by elastomeric element(s) such as an O-ring or flat washers or diaphragms may be nitrile rubber, silicone rubber, Viton rubber, latex rubber, EPDM or other elastic material;
sealing basic parts between assembling surfaces by adhesive materials such as UV curing adhesives or epoxy's and the like,
or combinations hereof.

In a first embodiment the invented Disposable Bioprocess System provides a container according to the invention manufactured from disposable materials suitable for micro-organism retention perfusion mode comprising in a liquid loop:
various ports arranged on said first container exterior wall for implementing sensors measuring process parameters;
further various tubes, hoses, ports pass though the outer wall of which some extending to and or from the first container interior volume for various fluid communication with external devices, such as a liquid suction tube for connecting to the second container operating as a SUP;
furthermore attending the first container a second tubular container operating as a SUP with a suitable interior volume comprising a first inlet port and a second outlet port and said container dosed with a bottom cover, a top cover and comprising a liquid level sensor;
furthermore attending the first container and second container arranged in liquid series a CFF device comprising a housing a micro porous internal separation wall a first inlet a second exit and a third harvest port;
furthermore attending the first and second container and CFF device arranged a first valve guiding broth in one direction from first container to second container and a second valve conveying broth in one direction from second container to CFF device and a liquid connection from CFF device in return to said first container closing the liquid loop.

In a second embodiment the invented Disposable Bioprocess System provides a first container suitable for micro-organism perfusion mode operation comprising:
various PG 13.5 ports arranged on the first container exterior wall for implementing sensors measuring various process parameters;
further various tubes, hoses pass though said first container exterior wall of which some extending to and or from the interior volume of said first container for various fluid communication with exterior devices;
a port arranged on the first container exterior wall furthermore for implementing a broth suction tube for conveying broth to a second container operating as a SUP. Said broth inlet from said first container comprising a suction tube inside first container is independent of penetrating said first container upper exterior wall the invented and presented Disposable Bioprocess System also becomes independent of the first container physical dimension—a valuable feature of the invention;
furthermore attending the first container a second tubular container operating as a SUP with a suitable interior volume comprising a first inlet port and a second outlet port and said container dosed with a bottom cover, a top cover and comprising a liquid level sensor;
furthermore attending the first container and second container arranged in liquid series a CFF device comprising a housing a micro porous internal separation wall a first inlet a second exit and a third harvest port;
CFF second exit port return processed liquid via a tube to first container completing the PTF concept;
CFF third outlet is considered harvest port;

SUP and CFF containers arranged independent of each other;

a liquid agitating impeller or turbine arranged on a shaft inside the reservoir of the first container said shaft driven in rotation by external means;

The first liquid conveying variation of the invented Disposable Bioprocess System takes advantage of a second container operating as the liquid broth conveying pump and arranged in series in liquid connection to said first container. The interior space of said second container represent a first liquid broth and a second drive gas compartment. The process broth arrives from the container and contain micro-organism and various debris. The second container being the SUP comprises:

a first inlet valve convey liquid from the first container liquid, broth reservoir;

a second outlet valve which convey liquid broth to the CFF device first inlet port;

a drive gas connection corresponding with external drive gas control means adjusting continuously the broth level height, the broth volume and velocity of the broth being conveyed by the pumping device in reciprocating action in a sequential though continues, one way, single direction liquid movement (opposite of alternating liquid movement which is dual-way liquid movement);

a SUP activity sensor—such as a liquid surface height measuring sensor, or a liquid volume measuring sensor, such a internal or external arranged Single-Use-Sensors or Re-Usable-Sensors.

Said CFF device second exit side corresponds with an optional third valve said third valve outlet which correspond with the first container process broth reservoir finalizing the closed liquid loop. The SUP container as well as the valves and the CFF device may be arranged outside or inside the SUB container. And more than one of each of the SUP and of the CFF may be integrated with or within the SUB. In any suitable combination and numbers promoting the process.

If desirable there may be a separating device between the drive gas compartment and the liquid broth compartment inside the second container. Such as a diaphragm, a piston, a discs, wet on one side and dry, semi-dry on the opposite side.

For the cultivation start a desired amount of media covering at least sensors and agitation devices in the SUB is inoculated according to the desired recipe. When desired biomass and WV has reached its potential the process is converted from batch to retention perfusion mode operation.

Perfusion process of this invention is the combination of several different operations modes, principles: 1. Cultivation mode (typically continues for weeks in the SUB), 2. Harvest—the "membrane conveying mode" at low velocity in CFF. 3. Deposit removal—the "membrane cleaning mode" at high velocity in CFF.

Different and independent operational modes following each other at desired intervals as described here:

process liquid of said SUB corresponds with one first valve insuring a one way, single direction fluid path from SUB to SUP;

said first valve corresponds with one associated liquid conveying SUP;

said liquid conveying SUP of variable capacity of/and pressure applied to the process broth conveyed from said SUB through said first valve;

said liquid conveying SUP convey process broth in one direction (not alternating) through a second valve and to the first inlet of said CFF device(s) and further through the CFF inlet channels, across the membrane;

to the retentate side of said CFF device(s) with volume and velocity though reduced pressure passing along the CFF device retentate membrane side to said CFF device opposite second outlet/end;

and said processed fluid returned to said SUB—when in membrane cleaning mode sequentially high velocity flushing removes the membrane fouling, deposits, which is returned to the SUB;

involving an optional third valve after the retentate/CFF exit when at least partly closed allow the liquid conveying SUP to apply higher pressure to the retentate side of said membrane(s) of said CFF device convey harvest through its pores by separating, avoiding micro-organisms and other particles from passing though said membrane said liquid when passed the membrane is considered to be the harvest or harvested product—when in membrane conveying mode;

said harvested product is separated from the permeate side of said CFF device and collected externally and forwarded to down-stream processing;

a volume from the cultivation broth (cell bleed) in said scalable Single-Use-Bioreactor is removed sequentially as waste in order to reduce the exponential growth and keep total desired bio mass at desired level;

a corresponding volume fresh media is added, replenished to the first container, SUB accordingly;

completing a cycle.

It is desirable to extent from the short SUB batch cultivation time (one week) and low micro-organism numbers high/bio mass (5-10×10E6 cells/millilitre. Practical PTF operational cell density range 20-100×10E6 cells/millilitre preferably measured with an on-line bio mass sensor. High cell density in general means higher productivity for the SUB. Longer cultivation time means more throughput, less time spend in starting the cultivation per run. A conventional batch process last one week plus one week for cleaning and process restart. It takes 7-10 days of batch cultivation before the PTF process can start. Continuous processing time of 5-6 weeks is relevant with 5-10 times the cell density to batch. With the present invention only one day is requited to start the next process. Compared batch against PTF then PTF is 30 times the amount of cells producing and product harvested.

The benefits of the second container representing the air column driven liquid conveying SUP (FIG. 1) are: low shear stress for the suspended cells, able to handle micro-carders, neither micro-carries or cells damaged now not passing a peristaltic pump, no problems with docking of the CFF as the setup is not a dead-end filtration, no alternating liquid flow, simplified operation, good control of liquid velocity and most important simplicity and of low cost allowing the SUP device to be designed from plastics and integrated fully and sterilized in the Disposable Bioprocess System.

General conditions for the first container, the SUB is that single micro-organisms may be kept in suspension or multiple micro-organisms aggregated in colonies kept in suspension or multiple micro-organisms adhered to micro-carriers kept in suspension.

A third embodiment comprises one or more containers if desired with different diameter and height and interior space volume. Either external to each other or the first container is arranged outside the second container which is here surrounding by the first container. The first container interior space contains process liquid broth including micro-organism and the second container being the SUP convey the broth and a third or optionally fourth containers being CFF devices. The second container interior space represent the air driven SUP pumping reservoir. The second container comprises a drive gas inlet, a first process broth inlet and a second process broth outlet. Said SUP first process liquid inlet correspond with the first SUB container reservoir via the first valve and the conveyed process liquid passing the second valve correspond via the second process liquid outlet corresponding with the first inlet of the broth side of a first CFF device. Said CFF device convey the broth to the retentate second exit returned to the SUB. Said CF device from its permeate third exit convey the micro-organism free liquid via appropriate connections with external means for harvest being withdrawn from the all sterile setup.

Supply of controlled sterile drive gas volume and pressure to the second SUP container head space allow pressure control of the head space volume above the process liquid broth. Controlling head space drive gas pressure controls the process liquid surface level height. As the process liquid level in the first container is lower than second container liquid level and process fluid must pass the first valve to be conveyed into the second container interior space volume this is all controlled by the second container head space gas pressure. Variation in head space gas pressure regulate the liquid level and combined with a optional third valve supply process liquid under TMP control for harvest. Or process fluid at high velocity for removal of deposit on the membrane surfaces on the retentate side. The CFF benefit from on its retentate outlet an optional controlled third valve with liquid outlet connected to the first container process liquid reservoir. When the third valve is opened the membrane cleaning pulse of high velocity liquid is returned, conveyed back to first container process fluid reservoir.

Bringing the perfusion process into operation require the first container hold the process liquid and the suspended micro-organisms for the cultivation as a broth. A least one CFF operate sequentially separating the micro-organism (or micro-carriers) from the process liquid and hereby keep the micro-organisms predominantly inside the first container interior space at any time. One or more SUP and one or more CFF may operate in parallel if desired and even with different specification and different control parameters.

It's end-user experience that the traditional and only commercial available stainless steel housing encapsulated CFF limits the process time as to extended membrane deposit issues. When the one and only CFF device module loose transport capability it is impossible to exchange the CFF and re-insert a new fresh CFF under sterile conditions.

The presented invention promote extended cultivation time by facilitating more than one pre-installed CFF internal as well as external to the first container. This feature allow users to extent the first container process operation time in perfusion mode by the number of connected, installed CFF modules.

The presented invention allow one liquid conveying second SUP container to be connected with one or more CFF devices. Performance of each CFF may be monitored continuously, such as by pressure drop (TMP) and mass flow sensors. The CFF may be of different size and different specifications. When the life time of the first CFF has reached a relevant upper limit of transmembrane pressure said CFF is blocked of by the third valve and the next and fresh CFF is brought into use—without risking/jeopardizing the sterile setup. The first and second valve preferably are low cost valves to be integrated in the invention. The third, fourth and more valves may be controlled hose/pinch valve allowing the complete process loop as presented in FIG. 8 to be pre-assembled and pre-sterilized hereby creating one sterile component fully eliminating further need for local sterilization.

In a fourth preferred embodiment (see FIG. 6) a free floating and non-controlled diaphragm based SUP is provided which convey broth from the SUB to and through the CFF. The SUP comprises two housing parts each with an interior chamber and groves for O-ring sealing on the circumference separated by and also sealed with when assembled by an elastic element. Said elastic element is a moulded thin flexible sheet integrated with a sealing O-ring on the circumference. Material preferably with compatibility with the requirement of the biological process. Upper single-use curved dome part comprises two ports; a first inlet port for SUB connection via a first one-way valve and a second exit port for CFF connection via a one-way valve. The lower potential re-usable housing part comprises a port for drive gas connection. Such as controlled drive gas pressure between vacuum and shop compressed air. The diaphragm have two positions being maximum expanded to each of the two end positions as determined by the two pump housing parts interior dimension.

The SUB is a container with magnetic agitation transfer through the bottom plate of the container. Various agitation devices may be added to the SUB such as the shown rotating shaft mounted with an impeller and driven by an external rotational force. A suction tube penetrate through the SUB wall into the SUB interior broth volume for suction of broth. The suction tube convey via a hose to a first one-way inlet valve located outside on the SUP dome to the SUP upper interior liquid chamber between the elastic diaphragm and the upper dome housing. The elastic diaphragm separate the sterile, wetted environment on the upper side and below the non-wetted non sterile drive gas compartment. The SUB suction tube ends into a hose which continues to the first valve inlet barb. The first valve allow one direction broth flow from the SUB into the SUP chamber. The second valve allow one direction broth flow from the SUP pumping chamber to the CFF inlet port. The CFF facilities the broth to pass along its channels to the CFF exit from which a hose insure the now retentate is guided back into the SUB and mixed with the broth finishing the liquid cycle.

Further in a fifth preferred embodiment (see FIG. 7) the SUP for combined SUB and CFF operation in a perfusion process setup is a diaphragm pump. An SUP example is described in WO2010/069321 being a free-floating and both in motion and position controlled elastic diaphragm is provided which convey broth from the SUB to and through the CFF. The SUP comprises two housing parts each with an interior chamber and groves for O-ring sealing on the circumference separated by and also sealed with when assembled by an elastic element. Said elastic element is a moulded thin flexible diaphragm integrated with a sealing O-ring on the circumference. Material preferably with compatibility with the requirement of the biological process. Upper single-use curved dome part comprises two ports; a first inlet port for SUB connection via a first one-way valve and a second exit port for CFF connection via a one-way valve. The lower housing part comprises a port for drive gas connection. Such as controlled drive gas pressure between vacuum and shop compressed air. The re-usable lower pump housing is equipped with a sensor for determining the position of the elastic diaphragm in real-time and possible 0.1 mm accuracy. Data from a position sensor will allow velocity and volume control of the SUP by modern electronics able to calculate input against PID algorithms and output for real-time regulating a proportional valve opening for variable drive gas pressure on the non-wetted side of the diaphragm. Said diaphragm will change position accordingly and respectively move a desired portion of liquid according to selected diaphragm position. The diaphragm based pump operate in series with valves and arranged between the SUB and CFF and with one first valve on the inlet side of the SUP and one second valve on the pump outlet side facing the CFF retentate inlet side. Optionally one third valve on the CFF outlet side for TMP control. The diaphragm pump collaborate and operated in series with the first and second valves. Which allow control of and insure one-direction flow being the invented PTF concept. The SUP control liquid volume and velocity of the broth through the CFF and volume of harvest and re-circulation volume on the retentate side of the CFF. Pressure is supplied by the SUP in order to overcome the gradually increasing TMP in the harvest situation. Broth velocity in order to sequentially flush out collected membrane deposit restoring CFF transmembrane pressure to its original stage.

Overcoming increasing TMP is established when the SUP is filled with process broth and the CFF is filled with process broth and first valve closed, second valve open and third optionally valve partly closed. Expanding controlled the diaphragm of said pump will increase system pressure and overcome TMP and the membrane will convey liquid and hereby converts retentate to permeate as the desired type of harvest.

One practical way of procedure is when the SUP diaphragm is in the relaxed stage and pump chamber and the CFF is filled with process broth and only the first valve is closed. The optional third valve arranged in the opposite end of the CFF, with relevance to the pump, is now open and allow high velocity liquid (like from 1 to 20 m/s) to be pumped with one or more pulses through the CFF. Said liquid broth pass the open third valve and return back into the SUB reservoir dragging along the collected cell material, deposit, etc from the CFF retentate membrane surfaces. The liquid loop is that all components is both supplied such as and operate in a closed loop. No alternating flow of liquids is required for membrane deposit removal. Only one liquid direction in the invented PTF setup hereby improve in general system and in specific the CFF performance as "fresh" process liquid broth is used for sequential membrane cleaning.

The SUP in the embodiment of a diaphragm pump is based on a flexible and/or elastic element being the diaphragm able to expand to a desired shape and/or return to a desired shape when exposed to as drive gas pressure ranging from vacuum to atmospheric overpressure. Movement of the flexible and/or elastic element with drive gas on one side and process liquid on the other side separates the non-sterile, non-wetted side with the wetted and sterile environment. Furthermore the diaphragm may take different shapes and be arranged anywhere outside as well as inside the container or part the rigid container wall or partially outside and inside on the container wall. The diaphragm may take shaped as a sheet of elastic material, shape as a sphere, shape partially as a sphere, shape as a tube, shape as a cylinder, shape partially as a cylinder closed in one end.

For the invented PTF the first and second valve may be a passive one-way valve know in the industry as umbrella valves or ball valves or buck bill valves. Or valves controlled by external means such as pinch valves or hose valves or sheet valves or poppet valves or combinations hereof.

The person experienced in working with membrane filtration know that deposits, debris, clogging is a significant problem. Deposits on elastic membranes may during the process be removed with controlled rapid changes in broth velocity. Pumps as used in cell retention CFF systems on the market from Spectrum Laboratories Inc, CA, USA and from Refined Technology (now Repligen Corp, MA, USA) do not allow rapid changes in broth velocities. Spectrum Laboratories use centrifugal pumps and Refined Technology a limited flexibility in movement diaphragm pump.

The present invention benefit from huge span in rapid broth velocity changes (measured in meter/second) passing along the CFF membrane surface. For harvest mode low velocities like from 0.01 to 1 m/s is sufficient. For cleaning cycles higher velocities will promote removal of deposits at 1 to 20 m/s or more. The SUP of the system are able to controlled alter velocity between the individual pumping cycles from lowest to highest velocity from one to the next pumping cycle. Hereby the expression "harvest cycle" and "cleaning cycle" is created. Utilising better CFF performance and longer process life time before the otherwise accumulating CFF deposits limit process performance and the cultivation is terminated.

Exchange of thermal energy of the media reservoir such as heating for cultivation and cooling for fermentation may be performed by encapsulating the SUB with heating blankets or water jacketed systems.

Thermal control can also be used to control the total biomass, cell density in the broth. As an example mammalian cell lines such as CHO cells operate at maximum cell growth rate at 37° C. They more or less divide once per 24 hours and hereby grow exponentially and will as to such eventually block the SUB. Reducing temperature with 3 to 10° C. will allow a stable cell density, cell population in the SUB such as 20 to 100×10E6 cells/millilitre for weeks.

Further desktop arranged parallel blocks, sockets, workstation, robots for insertion of the invented Disposable Bioprocess System will further give benefits such as easier sampling, simplified connection of the sensors to cabling and the associated PCS.

The parallel operating setup may take any shape facilitating the installed SUB bodies. SUBs may be arranged in one or more rows arranged in both directions creating assemblies with from 1 to 48 SUBs or more in one setup.

Alternating-Tangential-Flow DETAILS

The market dominating Alternating-Tangential-Flow concept "ATF" from Refined Technology is a dual flow direction, bi-directional flow concept in pulses. ATF offer reduced liquid exchange inside the Cross-Flow-Filter device as the CFF internal volume is not exchanged fully with fresh liquid at each stroke. Un-controlled dilution takes place inside the CFF.

The diaphragm pump of the ATF further offer only two positions for the elastic diaphragm. Two end positions and no positions in between allow no functionality as metering pump benefits except the total volume. The ATF diaphragm pump can only pump one specific volume being the particular pump size volume. As to this fact a range of pump sizes is required for different CFF sizes and different STRs. No valves are described in reference or used in practise for flow control or flow direction. The ATF concept pump do not allow programming for precise and selected pumped volumes for optimum perfusion performance and not combined with high velocities for controlled deposit removal prolonging the CFF lifetime.

ATF perfusion systems with cell retention CFF devices operate conventional glass/steel STR from 3 litre lab scale to 500 litre all steel production scale volume covered by 5 different pump sizes. The entire ATF selection of 5 pump sizes named ATF-2, 4, 5, 8, 10 cover a scalable factor of app. 1:55 over the entire range. The ATF pumps can only offer one full stroke in pumping capacity and not fractions of a stroke. Pump ATF-2 exchange 0.1 litre, ATF-4 exchange 0.4 litre—ATF 6 exchange 1.3 litre, ATF-8 exchange 2.5 litre, ATF-10 exchange 5.5 litre per stroke. Each of the 5 different pumps offer individual scalability of app 1:5 to STR volume. Each ATF pump must be connected to one specific size CFF with max ±10% surface area (app 0.1 or 0.75 or 2.5 or 4.2 or 10 m2) as to pump limitations. None of the ATF systems (pump housing, CFF housing, connections) is available in pre-assembled and pre-sterilised and disposable design. ATF is only available in stainless steel for manual mounting, insert of the CFF module, steam sterilization and rather complicated connection with the STR or large scale steel vessels.

Pulsating-Tangential-Flow DETAILS

In comparison the present PTF invention utilise one liquid flow direction, mono-directional, single flow direction in pulses. The present invention utilize the entire CFF broth volume exchange each time a pulse appear from the SUP. Fresh broth, liquid is always added to the SUP controlled by a valve. The present invention allow full control of velocity from 0.01 to 20 m/sec and volume performed by the SUP, when integrating a sensor.

The invented Disposable Bioprocess System operating in PTF mode take advantage of a variety of pump principles.

In the present invention the second container SUP (FIG. 1-5) is also a metering pump, when integrating a sensor, able to flow a desired and pre-controlled volume independent of time. The SUP can exchange a volume, such as the exact broth volume of the inside volume of the CFF at each pulse. With a stroke resolution of 0.1 mm and a 150 mm max stroke of the in FIG. 1 shown embodiment gives incredible 1:1.500 in volume variation in just one SUP size. Further one pump size will be able to satisfy the requirements of a very wide range of CFF modules with a factor 1:50 surface area and 1:50 range of SUBs which all reduce end-user investment.

Perfusion system (PTF) of the present inventions will allow SUB sizes down to 0.25 litre SUB laboratory scale W and up-scalable with impressive factor 500 with just one SUP size.

The present invention integrate a SUB with a SUP, a range of SUS, a single-use CFF, all hoses and all connections all fully pre-assembled, pre-sterilised and fully disposable for very simple and ease of use and much higher throughput at end-user site.

In the present invention the diaphragm pump (FIGS. 6 and 7) when integrating a sensor, utilise an extraordinary performance width in pumped velocity and measured volume. Able to flow a desired and pre-controlled volume independent of time, ranging from few ml/hour to litres per stroke. Each diaphragm SUP with diameter/volume, such as 100 mm/0.5 litre, 150 mm/1.7 litre, 220 mm/5.5 litre is capable of 1:5.000 in dynamic range. In principle requiring only one 220 mm SUP covering the entire CFF range from 0.1 m2 to 10 m2 surface.

Operation Methods

In general the 3 most used cultivation, fermentation and operation modes for a bioreactors or fermenters harbouring suspended micro-organisms as bio mass are;
 batch with constant Working Volume (WV) and one time harvest with typical 5 and if successful 10 mio cells/ml;
 fed-batch starting up with minimal WV and process media sequentially or continuous being added for exponential increasing bio mass in increasing Working Volume and one time harvest;
 perfusion with extraordinary high levels of typically suspended bio mass, connected CFF devices for high levels of micro-organism retention, sequentially Working Volume and sequentially or continues media exchange and continues harvest.

Perfusion cultivation—additionally, the experienced user will preferably use the invented Disposable Bioprocess System platform as a PTF perfusion mode operating SUB in which a desirable average amount of micro-organisms, bio mass are kept in cultivation. The expressed product is removed sequentially though under continuous harvest for further down-stream processing. The micro-organisms within the SUB continue to grow exponentially and continue to express their desired product. As to this on a regular basis an amount of broth including the cells must be removed from the SUB and fresh media added. This sequentially part of the process loose biomass and product, but is the accepted method. As to this the micro-organism retention perfusion process is not a continuous process performing at steady state conditions. One or more CFF devises are typically used for separation of the desired expressed product from the media WV containing concentrated micro-organisms, nutrients, waste, product, etc. The retentate concentrate is returned to the SUB after retention in the CFF. The CFF is sequentially exposed to the liquid feed stock, process fluid from within the SUB, which sequentially separate the suspended micro-organisms/the retentate from the harvest/permeate now free from suspended micro-organisms. The CFF devise (one or more than one) may preferably be of single-use character and integrated within the SUB and all components assembled together and supplied sterilized in dual film bags. Conveyance of micro-organisms containing media from the SUB WV through and along the one or more channels in the CFF devise may be performed by one or more fluid conveying SUP devices. Pressure difference along and across the CFF will insure liquids from the SUB WV are sequentially conveyed to and occupying the entire interior compartment of the CFF channels for purification.

The permeate side of the CFF may be either permanently or sequentially exposed for pressure lower than the (often atmospheric) pressure in the container. Removal of possible deposit/filter cake on the membrane surface is performed by rapid and or pulsating flow of liquid of such high velocity along the membrane surface that the particles adhering to the membrane is washed of, flushed back into the SUB container WV. Typical bio mass concentration for cultivation of mammalian cells with the cell retention systems here described range between 20 to 100×10E6 cells/millilitre or more.

The SUP is preferably also a disposable component and utilise a sensor able to give on-line information to a control device or a PCS, which can be used for velocity, volume and pressure control of said SUP. Preferable either a low cost SUS disposed with the invention or alternatively a high precision Re-Usable-Sensor. Good results have been obtained with a high precision tri-angular laser distance sensor able to measure between 30 and 200 mm length with resolution of 0.1 mm of the:
 dynamic liquid level height in the SUP tubular cylinder with better than 0.1 second response time;
 dynamic diaphragm position in the SUP body from beneath of the elastic diaphragm.

The SUP in a first embodiment and size as presented in FIG. 1 supplied with a suitable drive pressure of 1 to 8 Bar is able to perform from 1 stroke per hour to one stroke per second reaching 20 m/s velocity in this CFF examples being a hollow fibre module with 12 fibre tubes each 0.5 to 1 mm inside diameter and 400 mm long. Volumes ranging from few ml/hour to 150 ml/sec per stroke for the air column driven SUP as show in the FIG. 1 setup with 34 mm inner diameter tube. Hollow fibre tube specifications may be altered according to SUB volume and CFF surface.

Figure 6:
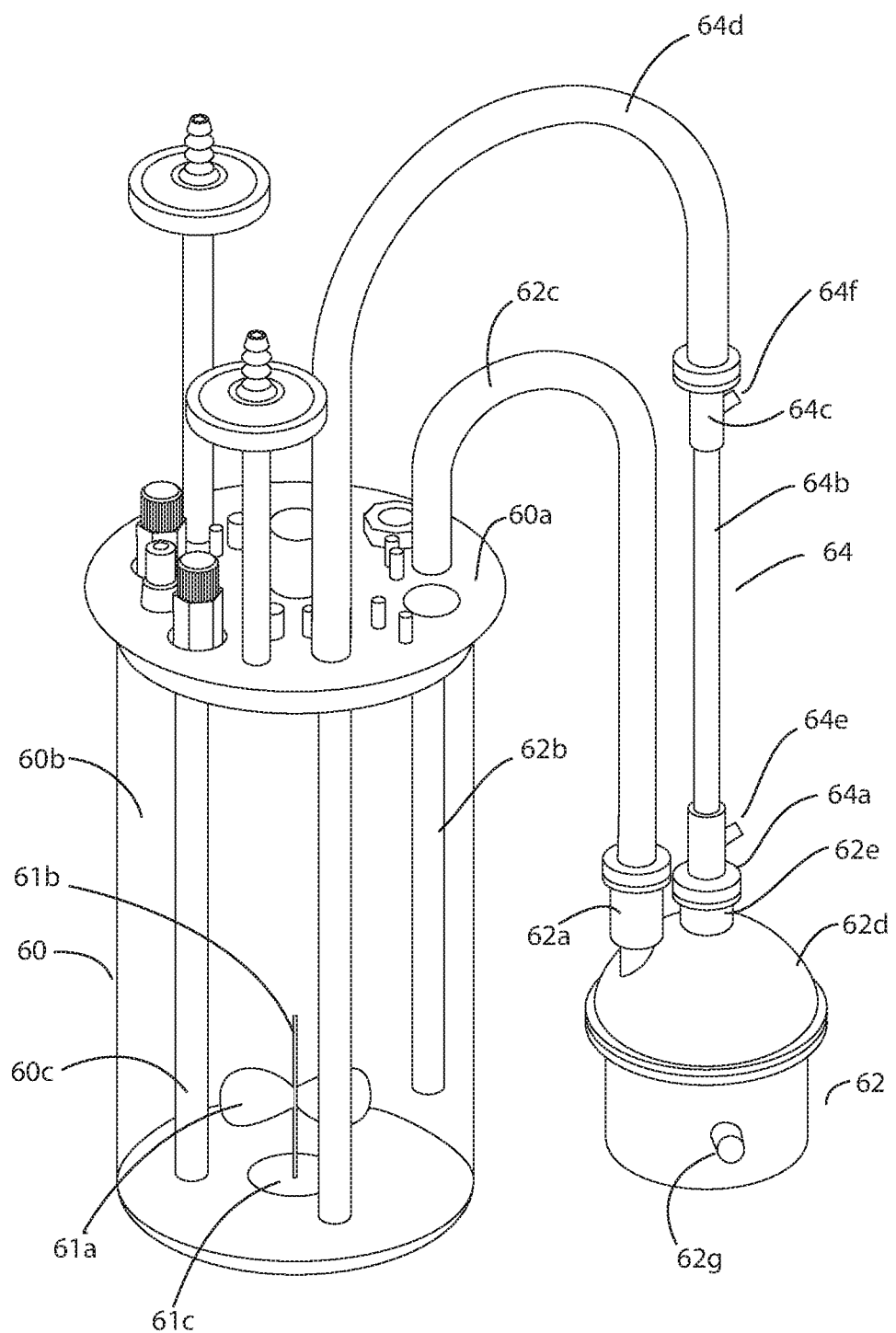
FIG. 6 show a PTF setup with a diaphragm SUP between a SUB and a CFF
Figure 7:
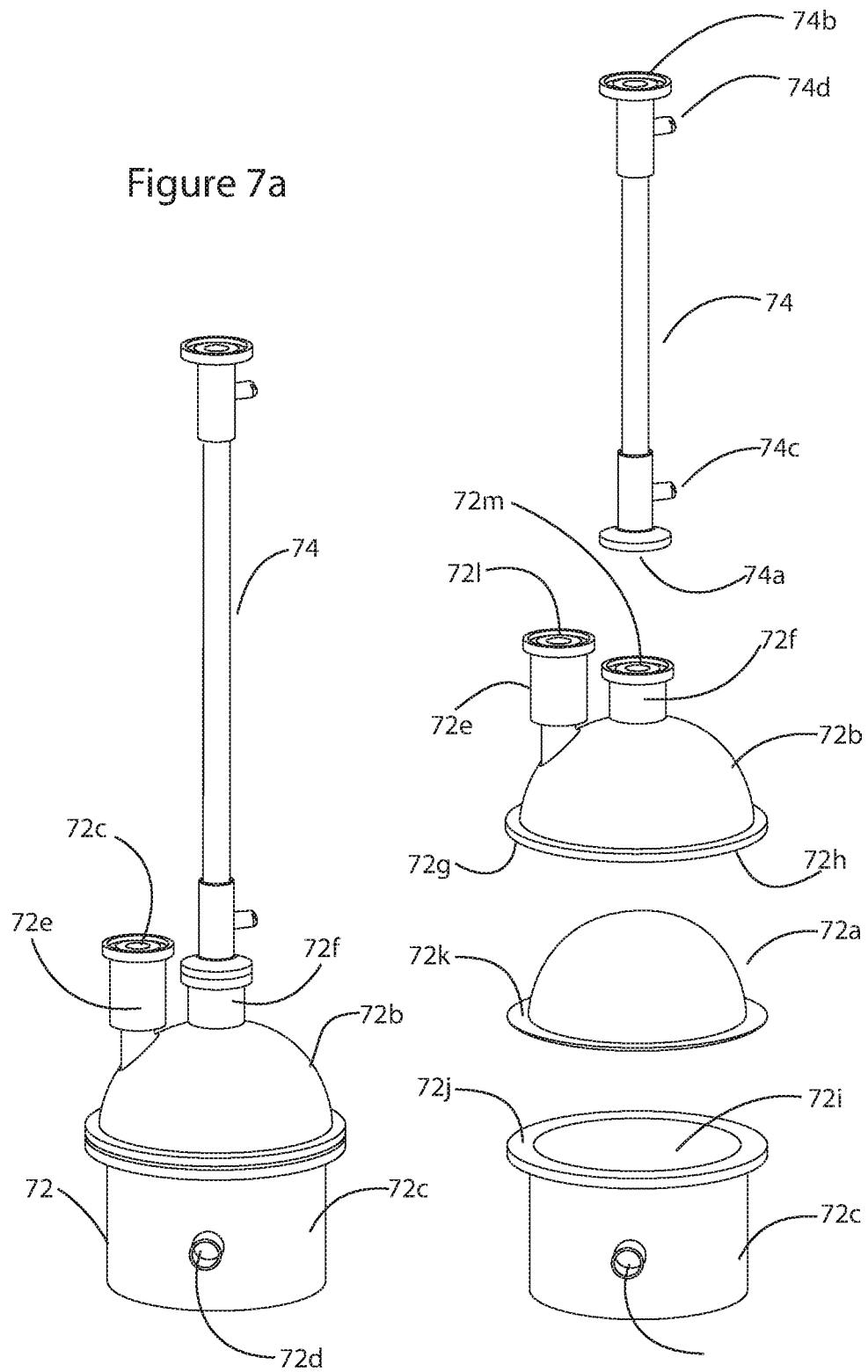
FIG. 7 illustrate a PTF pump with valves and a Cross-Flow-Filter mounted

The SUP in a second embodiment and size as presented in FIGS. 6 and 7 represents a precision pump able to convey a programmable volume at a programmable velocity. Supplied with a suitable drive pressure of 1 to 8 Bar the SUP is able to perform from 1 stroke per hour to one stroke per second reaching 0.01 to 20 m/s or more velocity in a connected CFF device. Volume depending on the diaphragm diameter and expansion rate and range from ml to litres per stroke.

Knowing the real-time position of a piston surface, liquid surface, diaphragm surface then simple mathematical calculation performed by a computer give accurate info about motion, velocity, volume ousted, etc.

Motion of said piston surface, liquid surface, diaphragm surface activated by drive gas pressure ranging from absolute to over atmosphere pressure. Pressure control by a pressure regulating valve, preferably a proportional valve. Said valve controlled by said computer or PCS.

The above described embodiments of the invented Disposable Bioprocess System are preferably connected to a PCS controlling the process variables and integrating the process information such as described in the process recipe:
  the PCS connected to multiple sensors integrated in said SUB and SUP and CFF from which the PCS continuously collects data of process variables;
  the Disposable Bioprocess System operational parameters are constantly altered by said PCS in communication with various actuators, devices integrated internally in said SUB, CFF and/or SUP or external to said Disposable Bioprocess System for process parameter control.

The PCS comprising controls for various In & Out channels such as:
  various electronic analogue as well as digital input channels for measuring, collecting data from a range of sensors;
  various pneumatic, gas, electronic analogue as well as digital output to a variety of actuators.

DESCRIPTION TO THE FIGURES

FIG. 1 illustrates in an x-ray view the invented sterile Disposable Bioprocess System 11 as supplied to the end-user fully assembled (here shown without a film protection bag). The SUB 12 container 12a include a sensor 13a, a sensor 13b and a biomass sensor 13c, twin impellers 17c, 17d mounted on shaft 17a, and one aeration tube 13e mounted through top cover 12b. The SUB 12 comprises a container 12a with vertical side wall 12c and inside the container a reservoir 12d and horizontal bottom wall 12e. The optional SUP suction tube 12f is connected via a 90 degree angled elbow arranged inside reservoir 12d and penetrating through the container 12a vertical side wall 12c via a port 12g to a first one-way SUP 15 inlet valve 14a before the SUP 15. The SUP 15 include an electronic liquid level/volume sensor 15a inside the SUP 15 housing 15b and a sterile filter 15c in series with the external and not shown drive gas control device. The CFF device 16 is arrange in series with and after a SUP 15 second one-way outlet valve 14d. CFF 16 receives the broth via SUP 15 second outlet valve. CFF 16 liquid retentate pass exit port 16b and is guided back to the SUB 12 via hose 16c and through SUB 12 vertical exterior side wall 12c inlet 16c and dumped in the SUB 12 broth reservoir 12d. The CFF 16 permeate outlet 16h and 16g, convey the product harvested through tube 16e and tune tube 16f. From the container 12a top cover 12b four externally arranged hoses 18a, 18b, 18c, 18d allow end-user to connect to external pumps and various media containers (not shown). The SUB 12 comprises a shaft 17a extending via a bearing 17e through the 30o top cover 12b into the container 12a, wherein said shaft 17a is equipped with means extending radially from said shaft 17a providing the agitation, such as one or more impellers 17c, 17d.

Figure 2:
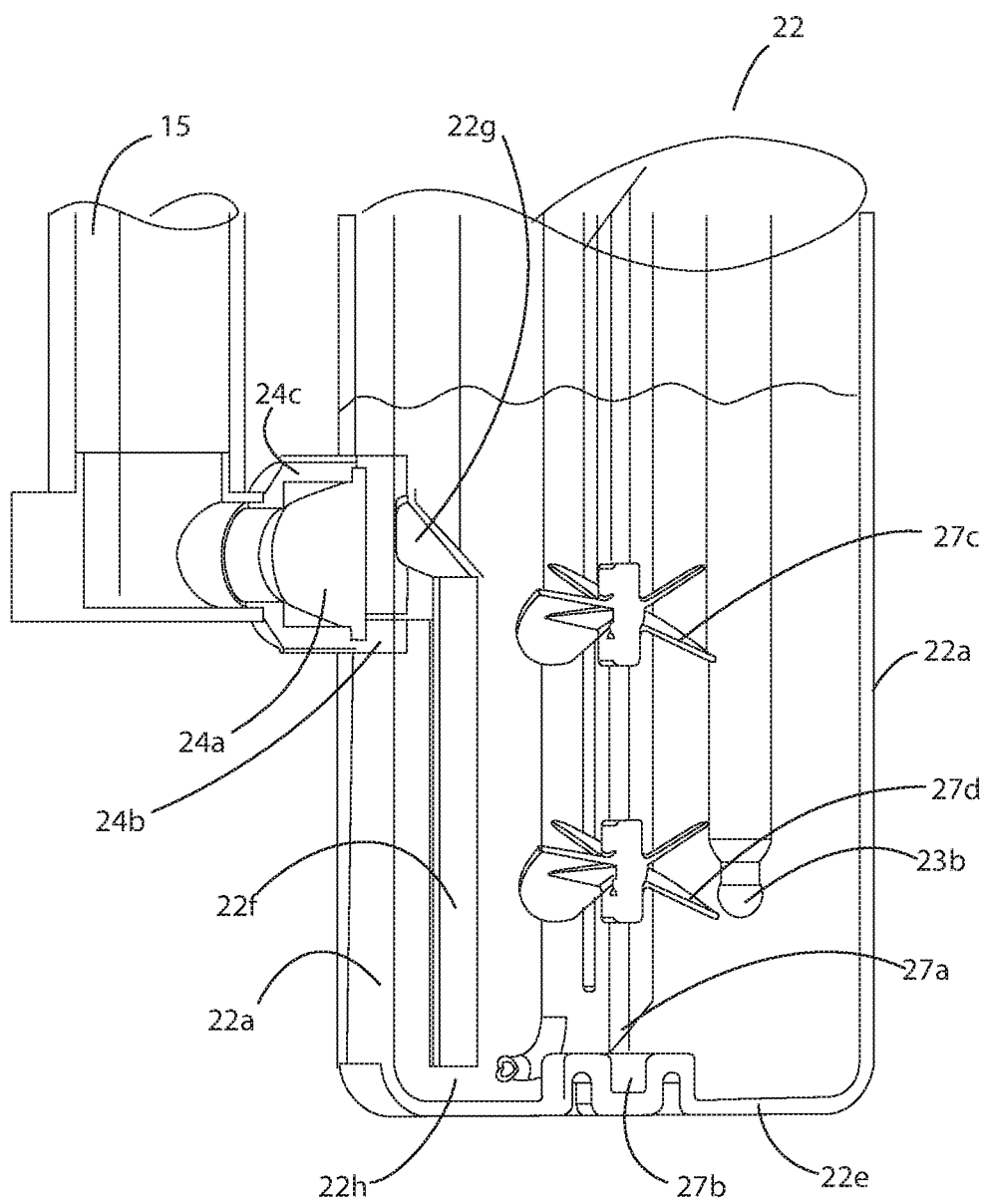
FIG. 2 show a tube penetrating the container vertical side wall

FIG. 2 illustrate with a cross sectional view of the lower part as a container 22 with a vertical container wall 22a and a supporting bearing 27b arranged in the container 22 bottom wall 22e into which a rotating shaft 27a is supported. Said shaft 27a is mounted with two impellers 27c, 27d. A PG 13.5 size sensor 23b tip is shown. A first valve body 24a is arranged on the exterior side of the container 22 vertical wall 22a between the top cover (not shown) and the bottom wall 22e. The valve body 24a is arranged between a first support foot 24b at container 22 interior side of wall 22a and a second support foot 24c at exterior side of container wall 22a. The assembly of inlet foot 24b and the inlet one-way valve 24 and the outlet foot 24c convey liquid media in one direction from reservoir 22d to SUP 15. The SUP 15 inlet 22f vertical arranged suction tube 22f is fixed at its top in an elbow 22g inside reservoir 22d and fixed onto the container interior side wall 22c in a suitable height from bottom wall 22e. The suction tube 22f extent freely hanging in a suitable distance 22h over the container interior side of bottom wall 22e.

Figure 3:
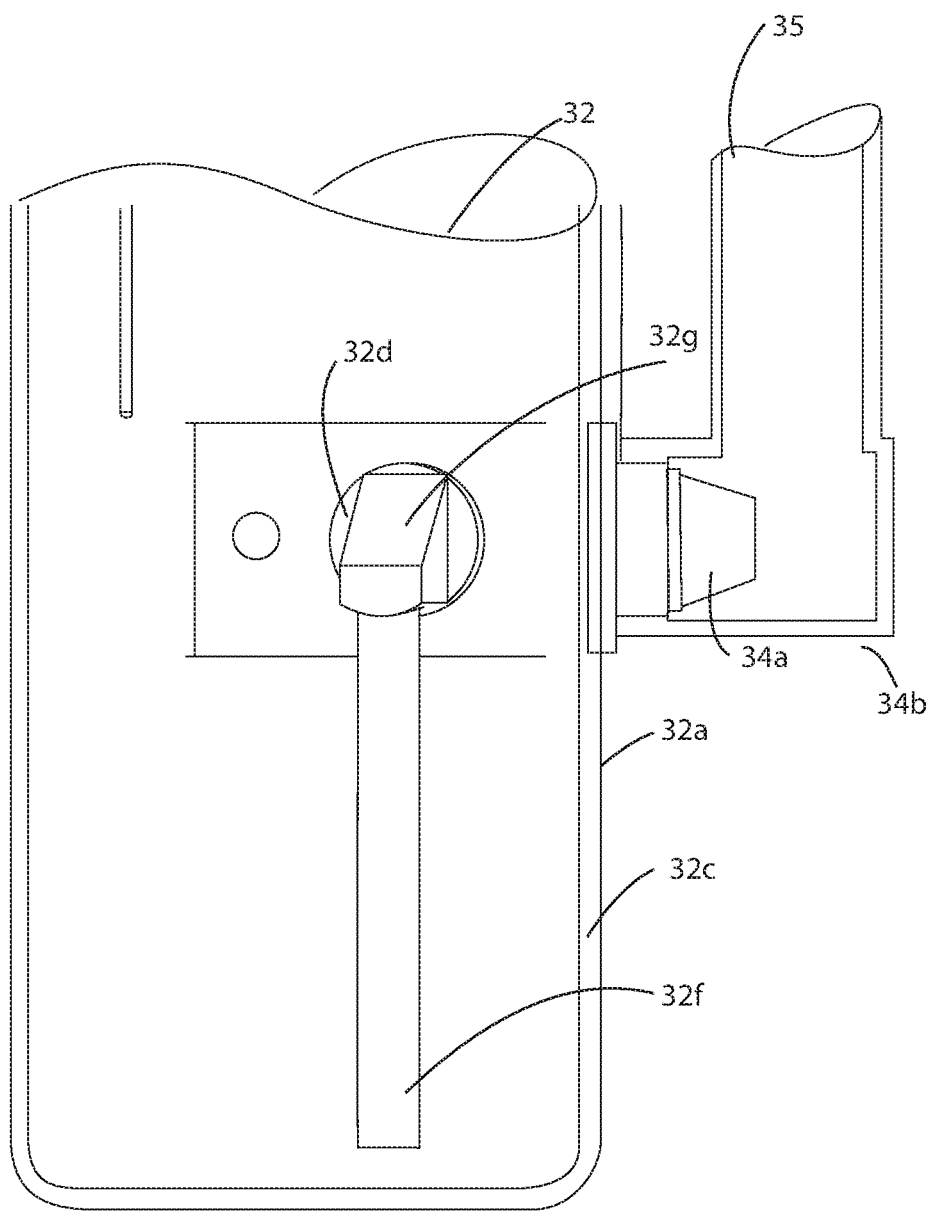
FIG. 3 show a tube penetrating the container vertical side wall

FIG. 3 illustrate with a cross sectional view a lower part of SUB 32 comprising a cylindrical container 32a. The vertical arranged suction tube 32f is fixed at the upper end in an angled elbow body 32g inside the container 32a onto the interior side of said container wall 32c. The suction tube 32f correspond through port 32d in the 20 container wall 32c with a first inlet valve 34a arranged inside support food 34b said support foot arranged on the exterior side of the container wall 32c. Support foot 34b further support the SUP vertical cylinder 35 on the upper exterior side.

Figure 4:
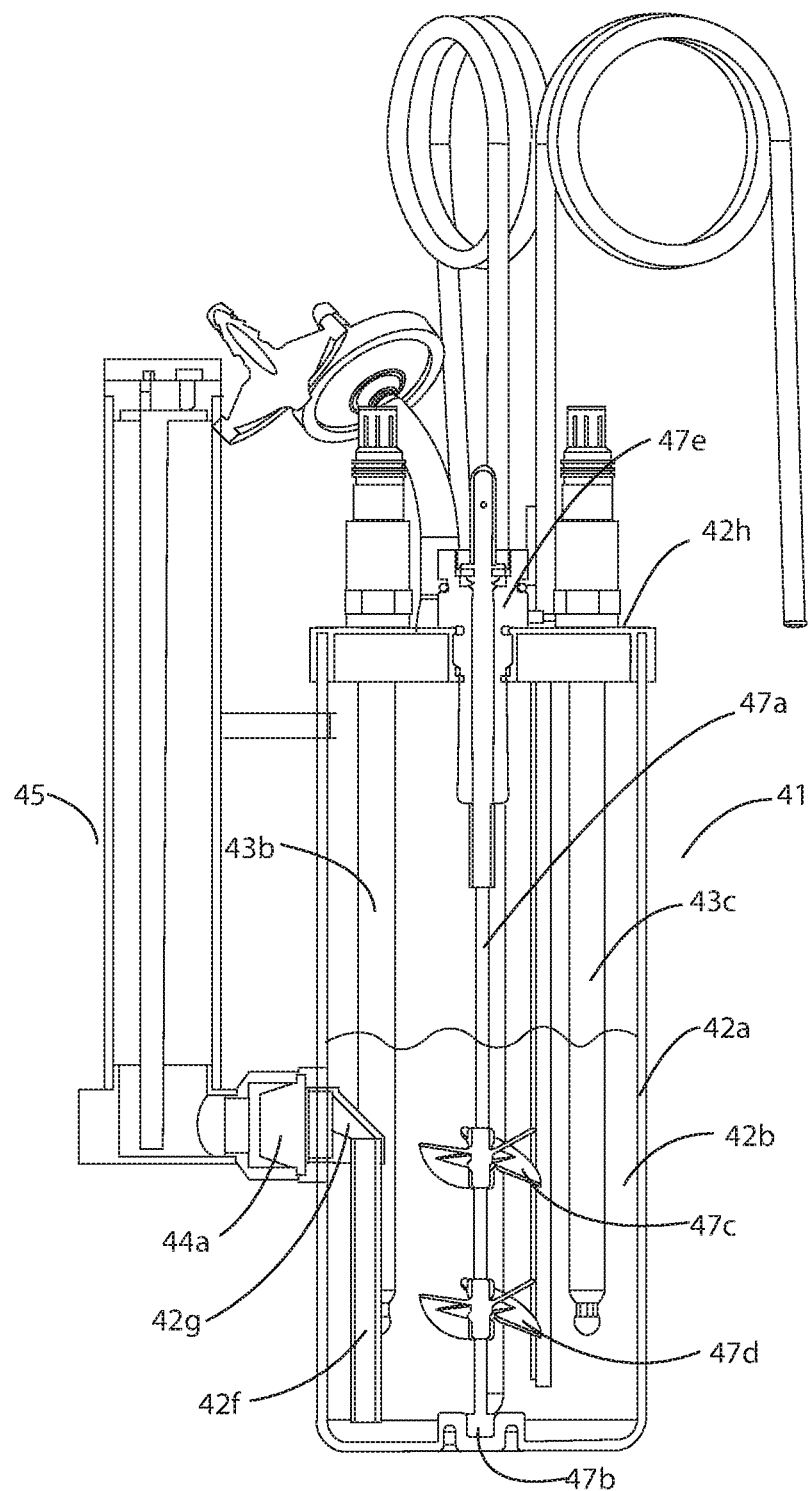
FIG. 4 show a tube connected to a one-way valve and a pump

FIG. 4 illustrate one embodiment of the present invention in a cross-sectional view of a PTF perfusion system with view of a SUB 41 with container wall 42a and a supporting bearing 47b at the bottom wall into which a rotation shaft 47a is supported. The shaft 47a is equipped with two impellers 47c, 47d and a Head-Plate-Drive bearing support 47e mounted in cover wall 42h facilitating an externally top mounted servo motor (not shown). A PG 13.5 based sensor 43b and a similar size biomass sensor 43c is shown extending into the broth reservoir 42b through the top cover wall 42h. A first inlet valve 44a body is shown arranged outside the container 42a exterior side wall between the SUP 45 and the SUB 41 insuring one way direction liquid flow drawn from the media reservoir 42b. The vertical arranged suction tube 42f is fixed in a 90 degree angled liquid conveying body 42g inside and onto the container 42a side wall. The SUP cylinder 45 in arranged external to the SUB 42 after the first inlet valve 44a and receive process broth passing the first inlet valve 44a from the media reservoir 42b inside SUB 41.

Figure 5:
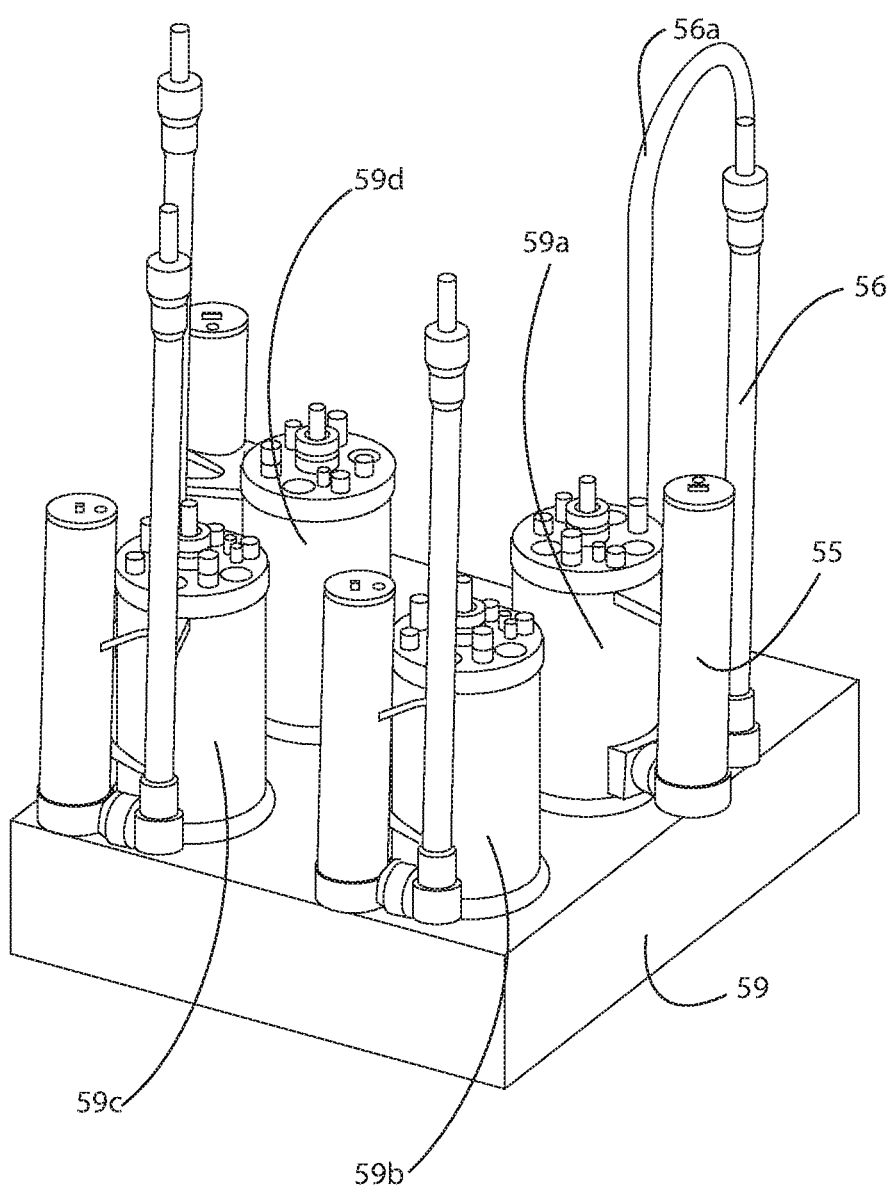
FIG. 5 show the invention mounted in a parallel operating Bioblock

FIG. 5 illustrate one embodiment of the present invention with one or more Disposable Bioprocess System's 51 installed in a block 59a designed for thermal control and mechanical support. If desired also for agitation purposes of one or more (59a, 59b, 59c, 59d) individual Disposable Bioprocess System's 51 being operated in parallel by a PCS (not shown). SUP 55 and CFF 56 shown installed on SUB 59a including only the CFF 56 return connecting hose 56a. All other hoses and accessories and sensors not show for simplicity.

FIG. 6 show an embodiment and the re-circulating liquid flow path in a PTF setup. A SUP 62 conveying broth between the SUB 60 and the CFF 64 and return the liquid to the SUB 60.

The SUB 60 container agitate continuously the liquid broth with an impeller 61a mounted on a shaft 61b driven by external means (not shown) said shaft attached to rotating magnetic device 61c. A suction tube 62b penetrate through the SUB 60 cover wall 60a into the SUB 60 interior liquid broth reservoir 60b. SUP 62 sucks liquid broth through a first valve 62a via tube 62d from SUB 60 liquid reservoir 60a and convey via hose 62c broth to said first valve 62a located on the SUP 62 dome wall 62d. Said first one-way valve 62a receive broth from SUB 60 and pass the broth volume further on to the internal pumping chamber of the SUP 62 when SUP 62 are in suction, filling mode. A second one-way valve 62e receive broth from SUP 62 outlet and opens and convey broth from SUP 62 internal pumping chamber when SUP 62 are in pumping mode. Port 62g allow drive gas to enter SUP 60 for operation purposes. Said broth pass on to CFF 64 broth inlet port 64a and said CFF 64 convey the broth along its internal porous membrane (not visible) inside the CFF 64 tubular container 64b in which the CFF 64 convert broth to both retentate and permeate. Said retentate of CFF 64 exit port 64c and is returned to SUB 60 via hose 64d closing the process liquid loop. Said CFF 64 allow an amount of the liquid broth to pass the CFF porous membrane through one of or both of the permeate outlet ports 64e, 64f. For simplicity only one sensor 60c is shown entering the container reservoir 60b through the cover wall 60a, other necessary hoses and sensors are not shown, no sensors inside SUP 64 is shown.

FIG. 7 show in 7a the SUP 72 assembled with CFF 74 connected and in 7b show the individual parts before assembling.

The SUP 72 comprises the expanded, curved elastic diaphragm 72a separating and suspended between the upper housing dome part 72b and lower housing part 72c. The dome 72b is secured mechanically with a coupling (not shown) to the re-usable SUP lower housing part 72c, which gives balance and support to the vertically arranged CFF 74. The SUP 72 facilitate a port 72d (62g) for the drive gas supply from external source (not show). The dome 72b exterior wall is equipped with the first inlet valve 72e housing and a second outlet valve 72f connected directly to the CFF 74 broth inlet port 74a. The curved single-use dome 72b is on the interior side of the flat circumference wall 72g attached fluid tight with a thin elastic curved diaphragm 72a separating the sterile, wetted environment 72h on the interior diaphragm side from the non-wetted non-sterile drive gas compartment 72i exterior side of the diaphragm. The SUB 60 suction tube 62b continuous into a hose 62c which continues to the SUP 62/72 inlet valve 62a/72e via first inlet port 72l. The first inlet valve 72e allow one direction broth flow from the SUB 60 into the SUP 62/72. The SUP 72 second outlet valve 72f allow broth in one direction to be conveyed from the SUP 72 pumping chamber 72h via second outlet port 72m to the CFF 74 first inlet port 74a. The CFF 74 facilities the broth to pass along its internal porous membrane surface (not shown) to the CFF 74 second exit port 74b from which a hose 64d insure the now retentate is guided, conveyed back into the SUB 60 reservoir and mixed with the broth finishing the PTF liquid cycle. A CFF 74 third and fourth permeate outlet ports 74c, 74d convey filtered process liquid to said exterior facility area as harvested product.

SUP 72 re-usable lower housing part 72c comprise a drive gas connection port 72d for controlled SUP 72 activity and a housing flange 72j suitable for gas tight connection with the diaphragm 72a circumference seal 72k.

Broth entering the SUP 72 pumping chamber 72h is enclosed, trapped between the elastic freely floating diaphragm 72a and the single-use rigid dome upper housing part 72b.

Figure 8:
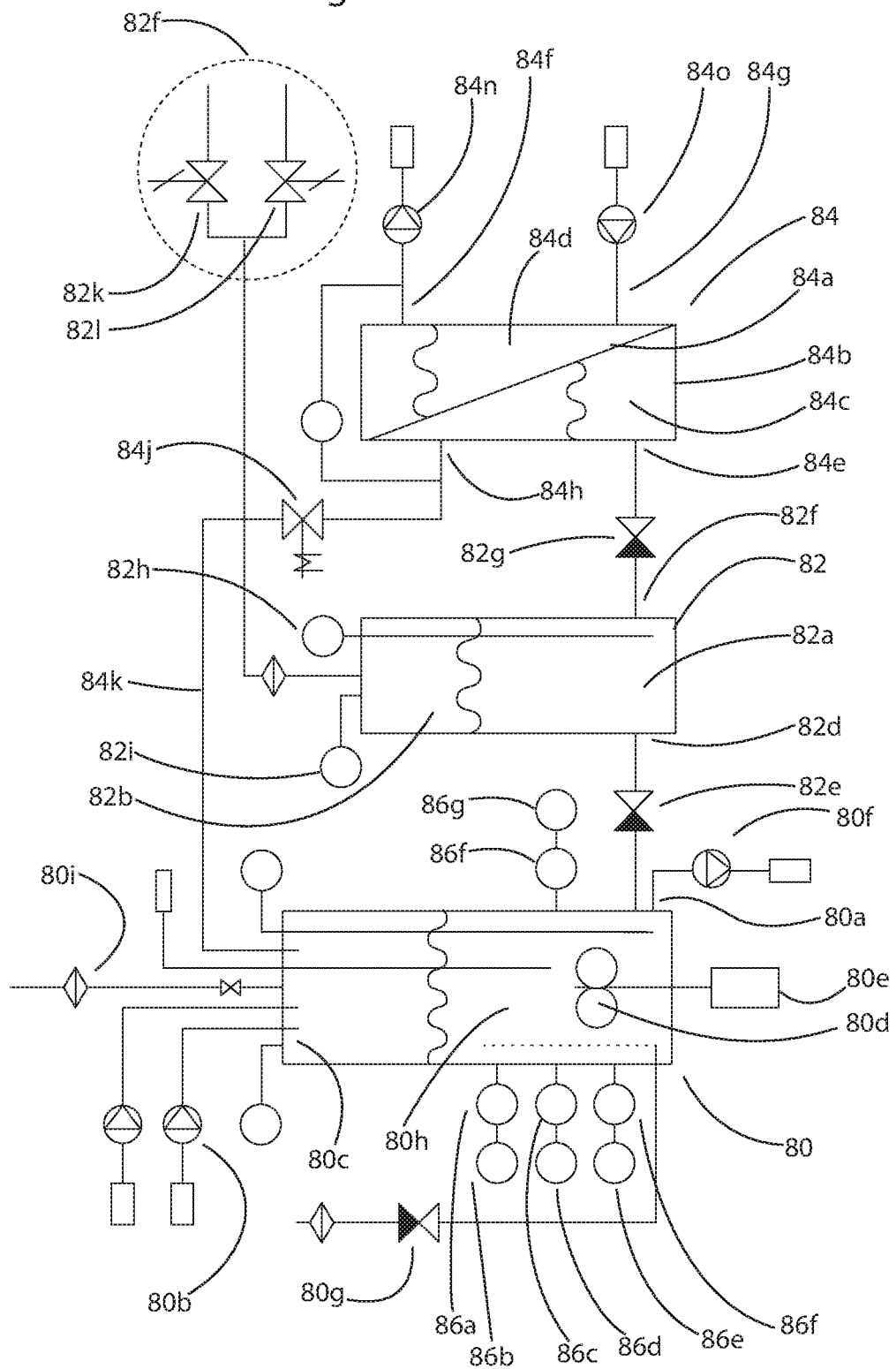
FIG. 8 illustrate a possible flow and process diagram

FIG. 8 block diagram illustrate and describe a relevant and practical flow diagram for a continuous cultivation and harvest process with a first container SUB 80, a liquid conveying second container SUP 82 and a third container CFF 84 in a closed process liquid loop.

The first container 80 house the biological activity process and convey cultivation broth to the second container SUP 82. The SUP pump broth to third container CFF 84 for separation into harvest and process liquid in return loop back to the SUB 80. The first container SUB 80 comprises a broth outlet port 80a, a fresh media pump 80b and inlet port 80c, an agitation device 80d driven by servo motor 80e, a Glycose sensor 86a, a Lactate sensor 86b, dual biomass sensor 86c, a pH sensor 86d, a dissolved oxygen sensor 86e, a 86f temperature sensor and SUB temperature controlled via heating element 86g. Fresh media is added via pump 80b and used media (including cells), waste removed via pump 80f. Aeration gas added to the SUB via control valve 80g and sparged into the process broth 80h liquid volume and exhausted out through vent filter 80i.

The second container SUP 82 houses the pumping process and comprises a broth volume 82a and a drive gas volume 82b. Drive gas inlet 82c, a first inlet port 82d associated with first inlet valve 82e, a second outlet port 82f associated with a second outlet valve 82g, a liquid sensor 82h, a pressure sensor 82i, a drive gas port 82j connected to external mounted dual proportional valves 82k, 82l (one valve for vacuum and one for pressure drive gas). The liquid sensor 82h give in real-time information to the PCS (not shown) about the liquid level height, which the PCS use to adjust SUP 82 drive gas pressure (from absolute pressure to over atmospheric pressure) via external dual valve arrangement 82k, 82l.

The third container CFF 84 houses the separation process and comprises a separating porous membrane 84a inside a CFF housing 84b with a broth side 84c and a permeate side 84d. CFF container 84 comprises a broth inlet port 84e and dual permeate outlet ports 84f, 84g and one retentate exit port 84h. Between permeate outlet port 84g and retentate exit port 84h a TMP sensor 84i is mounted. CFF 84 retentate exit port 84h guide retentate in process liquid loop to the SUB 80 and optionally use a control valve 84j in the retentate return line 84k for various process adjustments. Said CFF device 84 facilitate on its permeate side 84d one or more outlets 84f, 84g for product removal via optional controlled pumps (or optional valves) 84n, 84o.

In general, the mechanically design is unlimited and illustrated without any PCS or control package or external liquid reservoirs associated with the Disposable Bioprocess System embodiment.

While the present invention has been described in connection with particular embodiments thereof, it will be understood by those skilled in the art that many changes and modifications may be made without departing from the scope of the invention as defined by the appending claims.

I claim:

1. A Disposable Bioprocess System supporting biological activity comprising:
   a fluid tight container comprising a process liquid broth in an interior of said container surrounded by walls separating the process liquid broth in the interior of said container from an exterior facility area;
   a first liquid valve, wherein said process liquid broth communicates with said first liquid valve;
   an electronically controlled conveying liquid pumping device configured to pump the process liquid broth in one direction away from the interior of the container, wherein said process liquid broth communicates with said pumping device;
   a second liquid valve, wherein said process liquid broth communicates with said second liquid valve;
   a filter device separating the liquid process broth from the exterior facility area, said filter device being configured to receive and process said liquid broth into retentate and permeate and comprising a first broth inlet port, a second retentate outlet port, and a third permeate outlet port, wherein said process liquid broth communicates with said filter device, wherein:
      a means of liquid broth communication extending from the interior of said container to said pumping device;
      a further means of non-filtered liquid communication extends from said pumping device to said first broth port, said first broth port providing a non-filtered first liquid communication inlet port of said filter device,
      a further means for non-filtered retentate liquid extends from said second retentate outlet port to the interior of said container, said second retentate outlet port providing a second liquid communication exit port of said filter device through which non-filtered retentate is recirculated back to the process liquid broth in the interior of said container, and
      said third permeate outlet port communicates between said filter device and said exterior facility area for conveying filtered process liquid broth that has passed through the filter device to said exterior facility area as harvested liquid product;
   wherein the first liquid valve is positioned between said container and the pumping device and controls the communication between the process liquid broth of the interior of said container and the pumping device,
   wherein the second liquid valve is positioned between the pumping device and said filter device and controls the communication between the pumping device and said filter device, and
   wherein said container via at least one Single-Use-Sensor arranged in the process liquid broth measures at least dissolved oxygen and/or pH parameters for process control purposes.

2. The Disposable Bioprocess System of claim 1, wherein said container is a Single-Use-Bioreactor that comprises walls separating the interior process broth from the exterior area and a head plate wall, side walls, and a bottom wall opposite of said head plate wall, wherein a port is arranged in a wall of said container.

3. The Disposable Bioprocess System of claim 1, wherein at least one of the pumping device or the filter device is arranged inside said interior of said container.

4. The Disposable Bioprocess System of claim 1, wherein the pumping device with which the process liquid broth of the interior of said container communicates is an externally arranged pumping device, communication ports extend through a wall of said container, said pumping device communicates with said filter device.

5. The Disposable Bioprocess System of claim 1, wherein the pumping device with which the process liquid broth inside the interior of said container communicates is an internally arranged pumping device, pump communication ports communicate with said filter device.

6. The Disposable Bioprocess System of claim 1, wherein one or more ports are arranged in a wall of the container giving room for the at least one Single-Use-Sensors.

7. The Disposable Bioprocess System of claim 1, wherein the Disposable Bioprocess System is assembled from a part comprising, as said container, housing having a bottom wall and side walls that form an integral bottom and a head plate cover wall, wherein the head plate is assembled with the housing to form a closed and fluid tight container of the Disposable Bioprocess System.

8. The Disposable Bioprocess System of claim 1, wherein the container comprises a port arranged in a side wall and wherein the one or more ports allow for fluid communication between inside the interior of the container and outside of the container.

9. The Disposable Bioprocess System of claim 1, further comprising a rotating device inside the interior of the container, which is exposed to and surrounded by said process liquid broth, for supplying kinetic energy to the process liquid broth for agitating purposes.

10. The Disposable Bioprocess System of claim 9, wherein the rotating device comprises a shaft extending through at least one wall of the container into the process liquid broth, wherein said shaft is equipped with means extending radially from said shaft providing the agitation.

11. The Disposable Bioprocess System of claim 9, wherein the rotating device is attached to a shaft, said shaft comprises a magnetic component which interacts rotatingly with a rotating magnetic component drive source located outside of the container wall wherein a shaft is equipped with agitation means extending radially from said shaft providing the agitation.

12. The Disposable Bioprocess System of claim 1, wherein the means of liquid broth communication is equipped with a valve configured to convey process liquid broth between the interior of the container and the liquid pumping device and the filter device.

13. The Disposable Bioprocess System of claim 1, wherein the filter device is configured to receive and process said process liquid broth by a permeable membrane barrier and separation process into retentate and permeate.

14. The Disposable Bioprocess System of claim 1, wherein the pumping device comprises a process liquid inlet valve and at least one process liquid outlet valve, and said Disposable Bioprocess System comprises one or more pumping devices connected to a controlled drive gas supply for liquid volume alteration.

15. The Disposable Bioprocess System of claim 12, wherein said filter device is a Cross-Flow-Filter device that comprises a permeable membrane barrier with a retentate side and a permeate side, the first broth inlet port, the second retentate outlet port and the third permeate outlet port, and
   wherein said Cross-Flow-Filter device is in process liquid communication with the process liquid broth of the interior of said container, said Cross-Flow-Filter device separates micro-organisms contained in said process liquid broth from being conveyed through said permeable membrane barrier, said Cross-Flow-Filter device receives a through going pressurized process liquid broth on the retentate side of said permeable membrane, and said Cross-Flow-Filter device converts process liquid broth to micro-organism free harvest liquid product on the permeate side of said permeable membrane barrier.

16. The Disposable Bioprocess System of claim 1, further comprising integrating sensors for measuring at least one process variable selected from the group consisting of bio mass/cell density, capacitance, conductivity, dissolved carbon dioxide, lactate, glucose, glutamine, glutamate, ammonia, pressure, liquid level, fluid mass-flow, velocity, temperature, and viscosity.

17. The Disposable Bioprocess System of claim 1, wherein said Disposable Bioprocess System is made predominantly from rigid or semi-rigid plastic materials.

18. The Disposable Bioprocess System of claim 1, wherein said conveying liquid pumping device is a diaphragm pump comprising an elastic membrane where the position of the elastic diaphragm is measured continuously by a laser sensor with accuracy of better than 2 mm.

19. The Disposable Bioprocess System of claim 1, wherein the filter device is a Cross-Flow-Filter device.

20. A method for producing biological material by cultivating or fermenting micro-organisms in a biological process, comprising:
operating the Disposable Bioprocess System described in claim 1 in a continuous process mode and/or a perfusion mode and having the process liquid broth flow from the interior of fluid tight container through the pumping device and through the filter device, wherein the process liquid broth flows in one direction, and the Disposable Bioprocess System simultaneously expresses a micro-organism free biological material as the harvested liquid product.

21. A method of operating the Disposable Bioprocess System described in claim 1, comprising:
starting cultivation in the fluid tight container with a desired amount of process liquid broth covering that at least one Single-Use-Sensor is inoculated according to a desired recipe;
after a desired biomass and working volume has reached a maximum potential, converting the process from a batch to a perfusion mode;
operating the Disposable Bioprocess System in a perfusion mode, and controlling and adjusting continuously process variables of the Disposable Bioprocess system and integrating process information of the Disposable Bioprocess system with a Process-Control-System wherein:
said Process-Control-System connects to sensors integrated in said Disposable Bioprocess System from which the Process-Control-System continuously collects data from the process variables, and
said Disposable Bioprocess System has operational parameters that are constantly altered by said Process-Control-System in communication with the first liquid valve and second liquid valve and/or pumping device for process parameter control.

22. A method of operating the Disposable Bioprocess System described in claim 15, comprising:
starting cultivation in the fluid tight container with a desired amount of process liquid broth covering that at least one Single-Use-Sensor is inoculated according to a desired recipe;
after a desired biomass and working volume has reached a maximum potential, converting the process from a batch to a perfusion mode;
operating the Disposable Bioprocess System in a perfusion mode, and controlling and adjusting continuously process variables of the Disposable Bioprocess system and integrating process information of the Disposable Bioprocess system with a Process-Control-System wherein:
said Process-Control-System connects to sensors integrated in said Disposable Bioprocess System from which the Process-Control-System continuously collects data from the process variables, and
said Disposable Bioprocess System has operational parameters that are constantly altered by said Process-Control-System in communication with the first liquid valve and second liquid valve and/or pumping device for process parameter control,
wherein the Process-Control-System is configured to control two independent different and independent operational modes of the Disposable Bioprocess System: membrane cleaning mode for removal of deposits from the membrane and membrane conveying mode for harvesting of the biological material.

* * * * *